US010732180B2

(12) United States Patent
Rowlen et al.

(10) Patent No.: US 10,732,180 B2
(45) Date of Patent: Aug. 4, 2020

(54) UNIVERSAL CAPTURE ARRAY FOR MULTIPLEXED SUBTYPE-SPECIFIC QUANTIFICATION AND STABILITY DETERMINATION OF INFLUENZA PROTEINS

(71) Applicant: InDevR, Inc., Boulder, CO (US)

(72) Inventors: Kathy Rowlen, Boulder, CO (US); Laura R. Kuck, Boulder, CO (US)

(73) Assignee: INDEVR, INC., Boulder, CO (US)

( * ) Notice: Subject to any disclaimer, the term of this patent is extended or adjusted under 35 U.S.C. 154(b) by 103 days.

(21) Appl. No.: 15/315,680

(22) PCT Filed: Jun. 4, 2014

(86) PCT No.: PCT/US2014/040936
§ 371 (c)(1),
(2) Date: Dec. 1, 2016

(87) PCT Pub. No.: WO2015/187158
PCT Pub. Date: Dec. 10, 2015

(65) Prior Publication Data
US 2017/0199192 A1 Jul. 13, 2017

(51) Int. Cl.
G01N 33/569 (2006.01)
(52) U.S. Cl.
CPC ... *G01N 33/56983* (2013.01); *G01N 2333/11* (2013.01)
(58) Field of Classification Search
CPC .............................................. G01N 33/56983
USPC .......................................................... 506/9
See application file for complete search history.

(56) References Cited

U.S. PATENT DOCUMENTS

| 8,283,452 | B2 | 10/2012 | Kapteyn et al. | |
|---|---|---|---|---|
| 9,360,433 | B1 | 6/2016 | Rowlen et al. | |
| 10,261,081 | B2 | 4/2019 | Rowlen | |
| 2002/0160358 | A1 | 10/2002 | Schenerman et al. | |
| 2005/0214826 | A1* | 9/2005 | Mor et al. | G01N 21/05 435/5 |
| 2009/0124512 | A1 | 5/2009 | Rowlen et al. | |
| 2009/0163375 | A1 | 6/2009 | Bowman et al. | |
| 2009/0275016 | A1* | 11/2009 | Miller et al. | G01N 21/05 435/5 |
| 2010/0061990 | A1 | 3/2010 | Sasisekharan et al. | |
| 2011/0059472 | A1 | 3/2011 | Xuguang et al. | |
| 2011/0070574 | A1 | 3/2011 | Borg et al. | |
| 2012/0316079 | A1 | 12/2012 | Rowlen et al. | |
| 2013/0288922 | A1 | 10/2013 | Miller et al. | |
| 2016/0096882 | A1 | 4/2016 | Horowitz et al. | |
| 2016/0136262 | A1* | 5/2016 | Meijberg et al. | G01N 21/05 435/5 |
| 2018/0187273 | A1 | 7/2018 | Taylor et al. | |
| 2018/0330056 | A1 | 11/2018 | Stoughton et al. | |
| 2019/0003979 | A1 | 1/2019 | Rowlen et al. | |
| 2019/0376897 | A1 | 12/2019 | Smith et al. | |
| 2020/0011867 | A1 | 1/2020 | Rowlen | |
| 2020/0018749 | A1 | 1/2020 | Smolak et al. | |

FOREIGN PATENT DOCUMENTS

| JP | 2003009700 | 1/2003 |
|---|---|---|
| JP | 2003034588 | 2/2003 |
| JP | 2004510144 | 4/2004 |
| JP | 2006109746 | 4/2006 |
| JP | 2014527065 | 10/2014 |
| JP | 2016539314 | 12/2016 |
| KR | 10-2010-0074743 A | 7/2010 |
| WO | WO 2000/004389 | 1/2000 |
| WO | WO 2002/025287 | 3/2002 |
| WO | WO 2005/007677 | 1/2005 |
| WO | WO 2006/020126 | 2/2006 |
| WO | WO 2009/111865 A1 | 9/2009 |
| WO | WO 2009/148395 | 12/2009 |
| WO | WO 2011/050463 | 5/2011 |

OTHER PUBLICATIONS

Heil et al. (Influenza and Other Respiratory Viruses, 4, published online Oct. 12, 2010, pp. 411-416). (Year: 2010).*
Webster et al. (1979) Virol. 96(1):258-264.
Webster et al. (1981) J. Gen. Virol. 54(2):243-251.
Das Suman et al. (Mar. 13, 2013) Cell Host and Microbe. 13(3):314-323.
Supplementary European Search Report corresponding to European Patent Application No. 14893964.8, dated Nov. 27, 2017.
Bodle et al. (2013) "Development of an enzyme-linked immunoassay for the quantitation of influenza haemagglutinin: an alternative method to single radial immunodiffusion," Influenza Other Respir. Viruses. 7(2):191-200.
Fontana et al. (Sep. 1, 2015) "Influenza virus-mediated membrane fusion: structural insights from electron microscopy," Arch Biochem Biophys. 581:86-97.

(Continued)

*Primary Examiner* — Karla A Dines
(74) *Attorney, Agent, or Firm* — Leydig, Voit & Mayer, Ltd.

(57) ABSTRACT

A universal array for multiplexed quantification of variable hemagglutinin such as subcomponents of multivalent annual influenza vaccines that is robust to variations in proteins such as mutations and is capable of quantifying degradation of proteins. Universal capture array (100) comprises one or more substrates (102) and a low-density microarray (104) of sub-arrays (108) comprising spots (106*a-c*). The microarray (104) is contacted with one or more targets (202) at one or more unknown concentrations, and bound complexes (203) are formed and subsequently quantified with a suitable method. Quantified signals are compared to calibration curves to obtain one or more unknown concentrations and/or quantify degradation of the one or more targets (202). Other embodiments are described and shown.

23 Claims, 17 Drawing Sheets

(56) References Cited

OTHER PUBLICATIONS

Hashem et al. (2013) "A Novel Synthetic Receptor-Based Immunoassay for Influenza Vaccine Quantitation," PloS One. 8(2):e55428.
Kuck et al. (Aug. 1, 2008) "Photopolymerization as an innovative detection technique for low-density microarrays," BioTechniques. 45:179-186.
Kuck et al. (Oct. 20, 2014) "Titer on Chip: New Analytical Tool for Influenza Vaccine Potency Determination," PloS one. 9(10):e109616.
United States Food and Drug Administration (Aug. 2011) "A Strategic Plan: Advancing Regulatory Science at FDA," Regulatory Science.
International Search Report corresponding to International Patent Application No. PCT/US2014/040936, dated Oct. 27, 2014.
Meridian Life Science, Inc. (Oct. 4, 2017) "Certificate of Analysis," Catalogue No. C01318M. Lot No. 8J27717.
Meridian Life Science, Inc. (Nov. 6, 2017) "Certificate of Analysis," Catalogue No. C86304M. Lot No. 26K30717.
Rathore et al. (Nov. 2014) "Immunogen design for HIV-1 and influenza," Biochim. Biophys. Acta. 1844:1891-1906.
wikipedia.com (Aug. 14, 2013) "Linear Epitope," Wikimedia Foundation, Inc. Accessible on the Internet at URL: https://en.wikipedia.org/w/index.php?title=Linear_epitope&oldid=568513342. [Last Accessed Feb. 15, 2018].
European Search Report corresponding to European Patent Application No. 14893964.8, dated Mar. 8, 2018.
European Office Action, issued in EP14893964.8 dated Feb. 8, 2019.
Byrne-Nash et al. (Oct. 2018) "VaxArray potency assay for rapid assessment of 'pandemic' influenza vaccines," npj Vaccines 3:43, pp. 1-11.
Kuck et al. (available online Mar. 3, 2017) "VaxArray assessment of influenza split vaccine potency and stability," Vaccine 35(15), Apr. 2017: 1918-1925.
Kuck et al. (available online Apr. 23, 2018) "VaxArray for hemagglutinin and neuraminidase potency testing of influenza vaccines," Vaccine 36(21), May 2018: 2937-2945.
Australian Patent Examination Report No. 1 corresponding to Australian Patent Application AU 2012/271858, dated May 5, 2016.
Ekiert et al. (2009) "Antibody Recognition of a Highly Conserved Influenza Virus Epitope," Science 324(5924):246-251.
EP Office Action, dated Jun. 16, 2017, in European Patent Application No. 12 801 262.2, 6 pp.
EP Office Action, dated Jan. 22, 2018, in European Patent Application No. 12 801 262.2, 7 pp.
Indian Examination Report with English translation, dated Sep. 27, 2018, corresponding to in Application No. 10253/DELNP/2013, 7 pp.
Kingsmore (2006) "Multiplexed protein measurement: technologies and applications of protein and antibody arrays", Nature Reviews Drug Discovery, p. 1-11, published online doi:10.1038/nrd2006.
Korean Intellectual Property Office; International Search Report and Written Opinion of the International Searching Authority; dated Jan. 29, 2013; PCT/US2012/042093; 9 pp.
Krammer et al. (Oct. 2013) "Influenza Virus Hemagglutinin Stalk-based Antibodies and Vaccines," Current Opinion in Virology 3(5):521-530.
Liang et al. (2008) "Glycan arrays: biological and medical applications", Current Opinion in Chemical Biology, 12:86-92.
Liang et al. (2007) "Quantitative Analysis of Carbohydrate-Protein Interactions Using Glycan Microarrays: Determination of Surface and Solution Dissociation Constants," Journal of the American Chemical Society, 129:11177-11184.
Liu et al. (2006) "Validation of a Fully Integrated Microfludic Array Device for Influenza A Subtype Identification and Sequencing", Analytical Chemistry, 78(12):4184-4193.
LV et al. (2007) "High-thorough antibody microarrays for quantitative proteomic analysis ", Expert Rev. Proteomics, 4(4):505-513.
Minor (2010) "Vaccines against seasonal and pandemic influenza and the implications of changes in substrates for virus production," Clinical Infection Diseases 50: 560-565.
Nabel et al. (Dec. 2010) "Induction of Unnatural Immunity; Prospects for a Broadly Protective Universal Influenza Vaccine," Nature Medicine 16(12):1389-1391.
Robinson et al. (2002) "Autoantigen microarrays for multiplex characterization of autoantibody responses", Nature, 8(3):295-301.
Supplementary European Search Report corresponding to European Patent Application No. EP12801262, dated Dec. 4, 2014.
Townsend et al. (2006) "Experimental Evaluation of the FluChip Diagnostic Microarray for Influenza Virus Surveillance," Journal of Clinical Microbiology, 44(8):2863-2871.
Ueda et al. (1998) "Application of Subtype-Specific Monoclonal Antibodies for Rapid Detection and Identification of Influenza A and B Viruses", Journal of Clinical Microbiology, 36(2):340-344.
Vester et al. (2009) "Quantitative analysis of cellular proteome alterations in human influenza A virus-infected mammalian cell lines", Proteomics, 9:3316-3327.
Wang et al. (2002)"Array-Based Multiplexed Screening and Quantitation of Human Cytokines and Chemokines", Journal of Proteome Research, 1:337-343.
Wang et al. (2009) "Glycans on influenza hemagglutinin affect receptor binding and immune response", PNAS, 106(43):18137-18142.

* cited by examiner

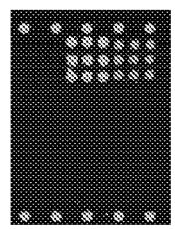 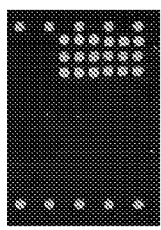 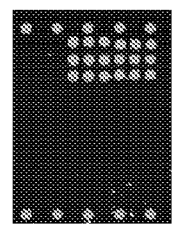 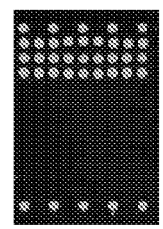 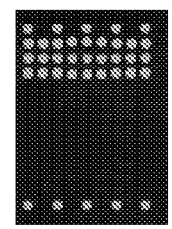
FIG. 7A  FIG. 7B  FIG. 7C  FIG. 7D  FIG. 7E
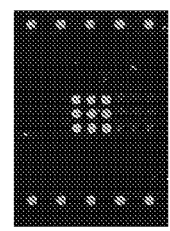 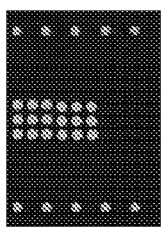 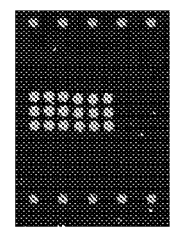 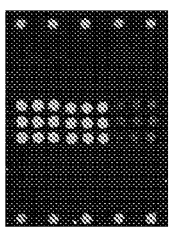 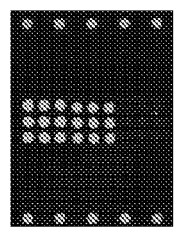
FIG. 7F  FIG. 7G  FIG. 7H  FIG. 7I  FIG. 7J
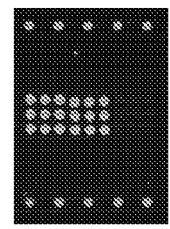 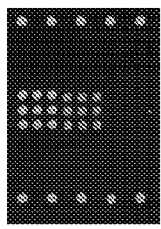 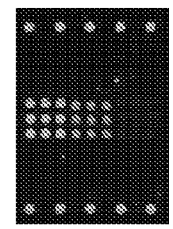 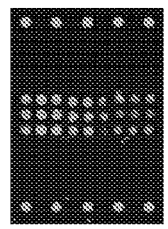 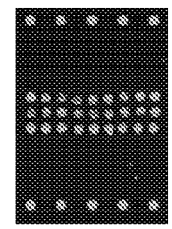
FIG. 7K  FIG. 7L  FIG. 7M  FIG. 7N  FIG. 7O
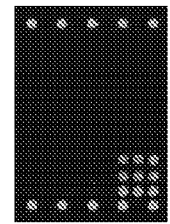 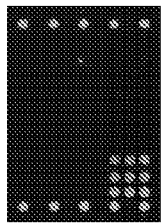 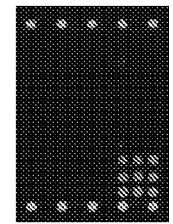
FIG. 7P  FIG. 7Q  FIG. 7R
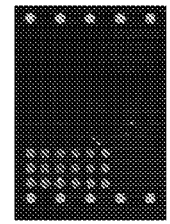 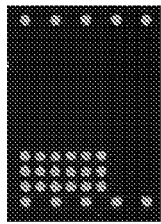 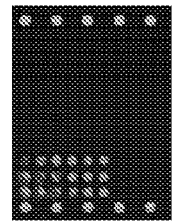 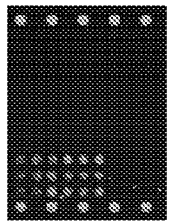
FIG. 7S  FIG. 7T  FIG. 7U  FIG. 7V

| Average Normalized Signal | Non-degraded | Degraded | Change (%) |
|---|---|---|---|
| Conformational | 19 ± 3 | 10 ± 2 | -53 |
| Linear | 16 ± 0.4 | 21 ± 0.8 | +30 |

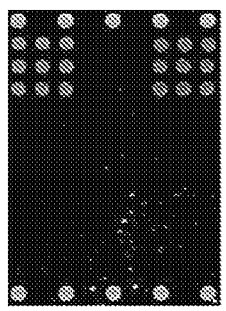 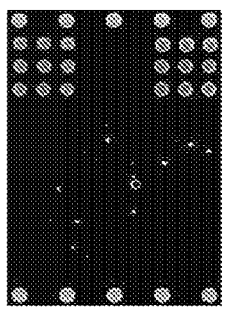 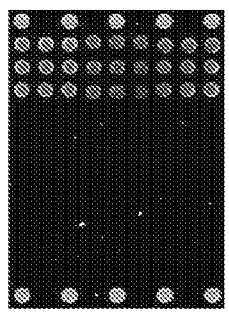 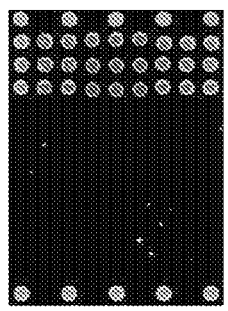
FIG. 13A    FIG. 13B    FIG. 13C    FIG. 13D
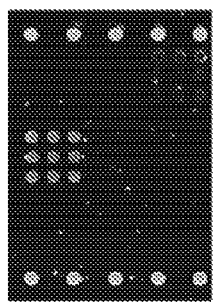 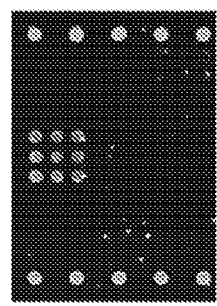 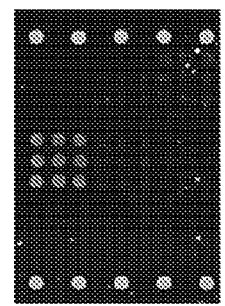 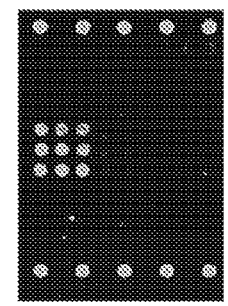
FIG. 13E    FIG. 13F    FIG. 13G    FIG. 13H
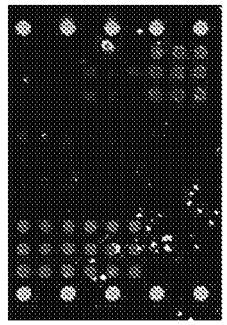 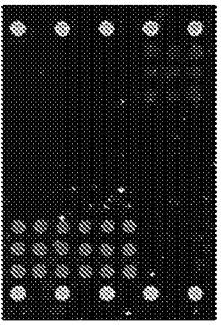 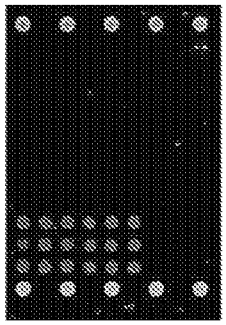 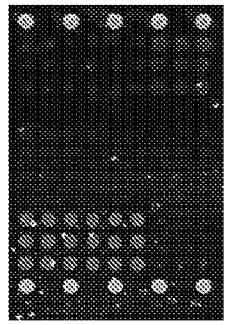
FIG. 13I    FIG. 13J    FIG. 13K    FIG. 13L
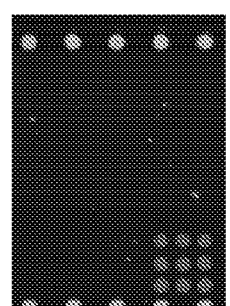 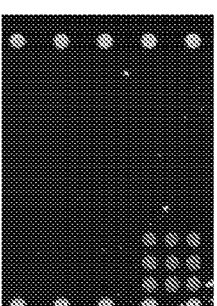 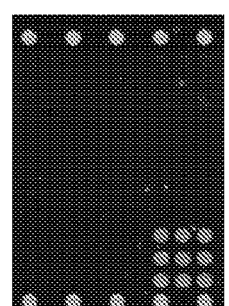
FIG. 13M    FIG. 13N    FIG. 13O

UNIVERSAL CAPTURE ARRAY FOR MULTIPLEXED SUBTYPE-SPECIFIC QUANTIFICATION AND STABILITY DETERMINATION OF INFLUENZA PROTEINS

STATEMENT REGARDING FEDERALLY SPONSORED RESEARCH AND DEVELOPMENT

This invention was made with Government support under GrantContract No, AI102318 awarded by NIH/NIAID. The Government may have certain rights in the technology of this patent application.

CROSS-REFERENCE TO RELATED APPLICATIONS

This application is a U.S. National Stage Application filed under 35 U.S.C. § 371 of International Application No. PCT/US2014/040936, filed Jun. 4, 2014, hereby incorporated by reference in its entirety.

BACKGROUND

The influenza virus poses a significant threat to global public health, and preemptive immunization by vaccination remains the most effective way to limit the impact of the virus. Vaccines against influenza comprise immunogenic material and may include one or more types of viral protein, including for example hemagglutinin (HA), neuraminidase protein (NA), or other viral material. One significant challenge for vaccination against influenza, however, is the frequent mutation rate of the virus.

Two key features of influenza vaccines directly result from the frequent mutation of the influenza virus. First, because multiple strains of influenza may circulate in a given season, modern vaccines are multivalent—that is, they contain antigens from multiple different influenza strains in order to confer immunity to multiple strains of the virus. Multivalent vaccines typically include HA and other viral proteins such as NA from three (trivalent) or four (quadrivalent) strains or subtypes. Current trends in vaccine development are towards developing higher valency vaccines, so as to confer the broadest possible immunity to those vaccinated. Vaccines with a valency as high as 7 have been reported. As a result, a modern vaccine may comprise a complex mixture of materials including agents for enhancing immune response (adjuvants), additives for preventing degradation of the formulation (excipients) and multiple varieties of HA and other immunogenically active proteins (e.g., NA).

The second feature of influenza vaccines that results from regular mutation of the influenza virus is that a new vaccine is generally developed each year. A strain predicted to dominate circulation in the upcoming season most often differs sufficiently from those of previous years to nullify the immunity conferred by prior vaccines, despite multivalency. In fact, a strain predicted to dominate circulation in the upcoming season (and so a component of the corresponding vaccine) may be different (e.g., a different subtype). For example, in one year a quadrivalent vaccine may be composed of influenza A HA subtypes 1 (H1) and 3 (H3) and two lineages of influenza B such as Yamagata lineage and Victoria lineage, while in the following year influenza HA subtypes 2 or 5 may be included instead of or in addition to H1 or H3. Influenza vaccines can thus vary significantly from year to year.

These characteristics of the seasonal flu vaccine impose enormous costs on the vaccine development process, in particular in quantifying the concentration of a new vaccine and its subcomponents, and in evaluating the stability of a new vaccine formulation. These costs represent open opportunities for innovation in developing improved quantification methods for the vaccine industry.

Desirable features for protein quantification in the vaccine industry include: being high-throughput and multiplexed to enable separate quantification of each of the components of a multivalent vaccine in a single test, being robust to changes in the target antigen so as to eliminate the requirement of corresponding changes in the reagents to adapt to seasonal HA mutations, and being capable of quantifying the extent of degradation of each component of a vaccine.

Currently, the only FDA- or WHO-approved method for protein quantification in influenza vaccines is the single radial immunodiffusion (SRID) assay. While widely adopted as a gold standard method, it provides none of the above mentioned desirable features: SRID is a low-throughput, singleplex method that requires new reagents each year to quantify antigen(s) in the current vaccine and is unable to adequately measure degradation. Also, SRID is a time- and labor-intensive assay that requires 2-3 days to complete and a minimum of 6 hours hands-on time by highly trained analysts. In addition, SRID is an expensive method, with costs of materials and labor for SRID analysis calculated to be approximately $1,000 per batch of 6 samples. SRID also employs subjective methods for readout and yields highly variable results. As a result, SRID is universally recognized as a significant bottleneck in the influenza vaccine development process, as evidenced by the FDA in, "A Strategic Plan: Advancing Regulatory Science at FDA" (2011). It is thus evident that SRID is not an adequate method for protein quantification in the vaccine industry.

One example method that significantly improves upon SRID is a microarray-based quantification method described in U.S. Patent Application Publication No. US2013/0494802 to InDevR, Inc. (2012). While this method is a much simpler and lower cost method than the SRID assay, it requires new reagents each year to detect and quantify antigen(s) in the current year's vaccine, and so it is not primarily concerned with variation or mutation in the target antigen. It also is not specifically designed to quantify protein degradation.

Others have attempted to provide robustness to mutations in the target antigen by using universal capture antibodies. Universal capture antibodies to HA are antibodies that bind to a highly conserved region of the HA and are thus expected to bind to most or all subtypes of HA, and most or all mutations of HA. For example, International Patent Applications PCT/IB2012/057235 to Novartis AG (2012), PCT/CA2009/000283 by Li, et al. (2009), and PCT/US2010/034604 to Sea Lane Biotechnologies (2010) describe various forms of universal antibodies and their uses. These capture agents are robust to seasonal changes in the target antigen and can be useful in the quantification of monovalent bulk material. Universal antibodies are severely limited, however, because by definition they are incapable of differentiating between strains and therefore cannot be used to quantify subcomponents of a multivalent vaccine. They therefore are of limited use for modern vaccine development and quality control. Universal antibodies also do not provide a method for quantifying degradation.

A similar, but more limited example of an attempt at universality is described in International Patent Application PCT/GB2012/052164 to Health Protection Agency (2012), which discloses methods for creating and using cross-reactive antibodies with quasi-universal binding. These antibodies are disclosed for use in singleplex quantification of potency of attenuated influenza vaccine (which consists mainly of attenuated whole virus, not free HA protein) using various singleplex methods such as ELISA, surface plasmon resonance (SPR) or the cumbersome SRID assay. The cross-reactive antibodies described by Hufton exhibit universal binding to a sub-group of HA, for example all HA belonging to a single phylogenetic group. However, these cross-reactive antibodies are not used to quantify more than one subcomponent of a multivalent vaccine in a single assay, and thus are not practical for use in quantifying trivalent or quadrivalent vaccines. The antibodies and methods described in the application also cannot be used to detect or quantify degradation of a vaccine.

In a related prior art example, International Patent Application PCT/US2001/028877 to Medimmune, Inc. discloses an in vitro, singleplex method for measuring the immunogenicity of vaccines based on virus-like particles that is intended to overcome the challenges of determining immunogenicity by immunizing mice. In the method a vaccine, having unknown fractions of an immunogenically active epitope and an immunogenically inactive epitope, is first immobilized directly and without use of a capture agent onto a solid support. The vaccine is subsequently labeled in this immobilized and non-native state by two antibodies, each labeled by a different fluorophore, one of which binds to the immunogenically active epitope of the immobilized vaccine and the other of which binds to the immunogenically inactive epitope of the immobilized vaccine. Quantification of the relative amount of immunogenically active epitope of the vaccine in its immobilized and non-native state is used as a predictor of vaccine immunogenicity. This method is limited, however, in that it requires that a vaccine have both immunogenically active and inactive epitopes. This method is further limited because it requires that the vaccine, having unknown fractions of immunogenically active and inactive epitopes, be immobilized directly and without use of a capture agent onto a solid support prior to quantification of the fractions of immunogenically active and inactive epitopes. The immobilization of a protein directly and without use of a capture agent onto a solid support is well known to denature a significant fraction of the protein, so that subsequent quantification of the relative fraction of denatured and native protein as the method requires is rendered inaccurate. Because the relative amounts of immunogenically active and inactive epitopes in the vaccine are initially unknown in this method, the deleterious effects of immobilizing the vaccine directly and without capture agent onto the solid support cannot be accounted for in the measurement by calibration. Therefore the method described in PCT/US2001/028877 to Medimmune, Inc. is inaccurate. In addition, the pair of monoclonal antibody labels described bind to the epitopes with high specificity and could not be used to quantify immunogenicity of a different vaccine, including for example a seasonally-mutated variation of the same antigen if the seasonal mutation had altered the binding epitope significantly, as is common. The method disclosed in PCT/US2001/028877 to Medimmune, Inc. is further limited because it is a singleplex method in which the vaccine sample is immobilized on a single substrate and multiple labels are bound in the same region, prohibiting the multiplexing of the method to enable quantification of the immunogenicity of the subcomponents of a multivalent vaccine in a single reaction. Thus the method described in PCT/US2001/028877 to Medimmune, Inc. is not practical for use in the modern vaccine industry.

Thus, there is a significant need for improvements to the technology for quantification of antigen(s) in vaccines. In particular there is a significant need for a multiplexed quantification method that is able to differentiate and quantify sub-components of multivalent vaccines, that is able to quantify antigen(s) in the current annual vaccine without requiring different reagents be used for each possible mutation (e.g., seasonal), and that is able to measure degradation of the sample without the need for a reference, non-degraded sample. This new protein quantification method should also be more reliable and simpler to perform than the current SRID method, with comparable or better accuracy and precision.

SUMMARY

In accordance with one aspect of the technology of the present application, a molecular capture array and method comprise a universal quantification, subtyping, and evaluation of degradation of variable proteins.

This summary is provided to introduce a selection of concepts in a simplified form that are further described below in the Detailed Description. This Summary, and the foregoing Background, is not intended to identify key aspects or essential aspects of the claimed subject matter. Moreover, this Summary is not intended for use as an aid in determining the scope of the claimed subject matter.

Accordingly, several advantages of one or more aspects of the technology over conventional hemagglutinin (HA) quantification methods include, but are not limited to, the following: to provide a multiplexed protein quantification method that enables differentiation and quantification of sub-components of a protein mixture such as a multivalent vaccine with a single test, to provide a universal method for detecting and quantifying variable HA, for example seasonally mutating HA protein, without requiring that reagents such as antibodies be changed, to provide a multiplexed method for the quantification of degradation of HA that may be a subcomponent of a protein mixture, to eliminate the requirement that SRID be performed to quantify HA in a vaccine, to provide a low-cost, simple method for HA quantification that can be performed by a user with minimal technical expertise and that reduces hands-on time, to increase objectivity in protein quantification, to simplify HA quantification and reduce costs, to provide a HA quantification technology that is more reliable and simpler to perform than SRID. The technology of the present application in one or more aspects provides a universal microarray to enable the multiplexed quantification of variable hemagglutinin proteins. Other advantages of one or more aspects will be apparent from a consideration of the drawings and ensuing description.

BRIEF DESCRIPTION OF THE DRAWINGS

Non-limiting and non-exhaustive embodiments of the technology of the present application, including the preferred embodiment, are described with reference to the following figures, wherein like reference numerals refer to like parts throughout the various views unless otherwise specified.

FIGS. 7A-7V show fluorescence signals generated at spots of a universal capture array of FIG. 1 when exposed to a variety of subtypes, and strains of influenza hemagglutinin.

FIGS. 13A-13O show fluorescence signals generated at spots of a universal capture array of FIG. 1 when exposed to recombinant hemagglutinin from four subtypes and lineages of influenza: A/CA H1 (FIGS. 13A-13D), ATX H3 (FIGS. 13E-13H), B/Mass/Yamagata-like (FIGS. 13I-13L), and B/Bris/Victoria-like (FIGS. 13M-13O) at four different stages of a typical vaccine manufacturing process: at the crude extract stage (FIGS. 13A, 13E, 13I and 13M), after process intermediate 1 (FIGS. 13B, 13F, 13J and 13N), after process intermediate 2 (FIGS. 13C, 13G and 13K; no sample corresponding to B/Bris/Victoria-like was obtained at this stage), and in the bulk drug substance form (FIGS. 13D, 13H, 13L and 13O).

DETAILED DESCRIPTION

The technology of the present application will now be described more fully below with reference to the accompanying figures, which form a part hereof and show, by way of illustration, specific exemplary embodiments. These embodiments are disclosed in sufficient detail to enable those skilled in the art to practice the technology of the present application. However, embodiments disclosed herein may be implemented in many different forms and should not be construed as being limited to the embodiments set forth herein. The following detailed description is therefore, not to be taken in a limiting sense. Moreover, the technology of the present application will be described with relation to exemplary embodiments. The word "exemplary" is used herein to mean "serving as an example, instance, or illustration." Any embodiment described herein as exemplary is not necessarily to be construed as preferred or advantageous over other embodiments. Additionally, unless specifically identified otherwise, all embodiments described herein should be considered exemplary.

Figure 1:
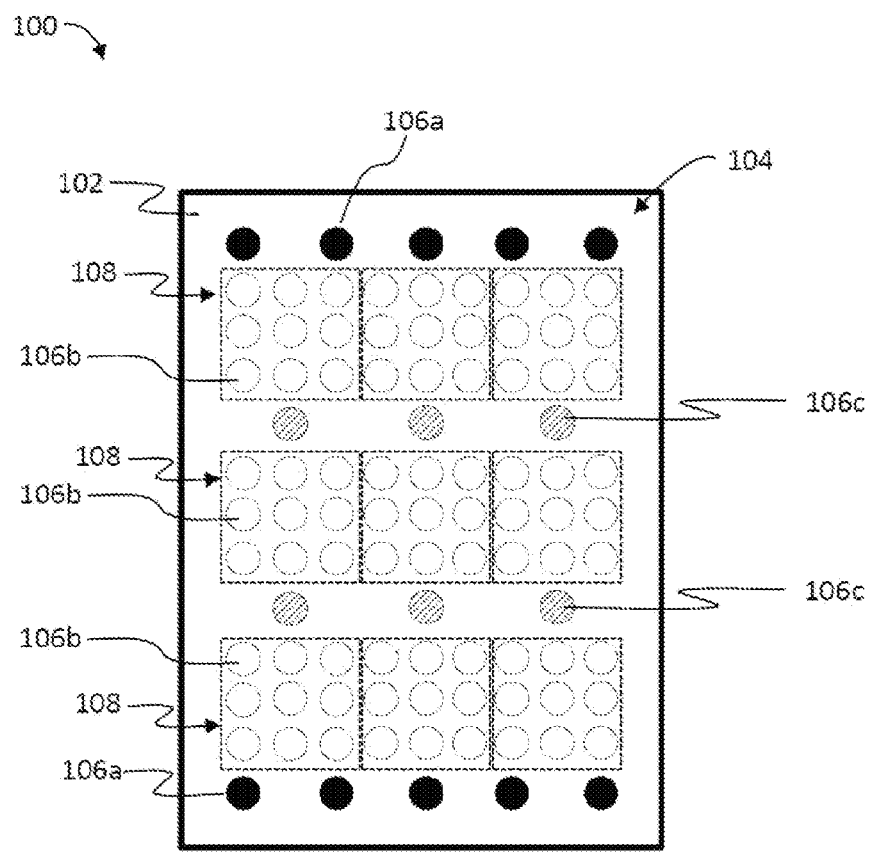
FIG. 1 shows a schematic illustration of a universal capture array according to one embodiment of the present disclosure.

In one embodiment, the present disclosure provides a universal capture array such as universal capture array 100 illustrated in FIG. 1. The universal capture array 100 comprises a substrate 102 which includes a low-density microarray 104 comprising a plurality of spots 106a-c, which are spatially distinct from one another. In some embodiments, spots 106a, 106b and/or 106c are arranged on the substrate 102 in patterns. For example a plurality of spots 106a, 106b and/or 106c may be grouped into one or more sub-arrays 108. As shown in FIG. 1, in one embodiment a universal capture array may include nine sub-arrays 108 (broken lines), with each of the sub-arrays 108 including nine spots 106b.

In one embodiment, substrate 102 is a conventional microarray print substrate, for example a Type H slide made by Schott. However, substrate 102 can consist, consist essentially of, or comprise many other materials with consideration taken for chemical composition of the print surface, print quality and repeatability, background signal, signal measurement method, cost and ease of use. For example, substrate 102 may be a flat glass slide with an epoxy coating or other appropriate coating a membrane or flexible membrane, a slide with a hydrogel coating, a plastic, a semiconductor, or a variety of other appropriate substrates known to one skilled in the art. In another embodiment, substrate 102 may be an appropriately functionalized glass or plastic microsphere.

Each spot 106b of microarray 104 comprises, consists of, or consists essentially of a single murine antibody capture agent. In one embodiment, capture agent spot 106b comprises, consists of, or consists essentially of a murine antibody targeting a conformational epitope of an influenza hemagglutinin. In some embodiments, the influenza hemagglutinin comprises, consists of, or consists essentially of influenza hemagglutinin from strain A/Victoria/361/2011. In some embodiments, capture agent spot 106b further comprises, consists of, or consists essentially of a molecular capture agent used to characterize the quality of printing or variations in printing. For example and without limitation, the molecular capture agent may include small molecules, lectins, antigens, nucleic acids, cells or fragments of cells, virus particles or fragments of virus particles, and/or combinations thereof.

In some embodiments, the microarray 104 comprises one or a plurality of negative control spots 106c. In some embodiments, the microarray 104 comprises 1 to about 20 negative control spots 106c, for example 1 negative control spot 106c, 2 negative control spots 106c, 3 negative control spots 106c, 4 negative control spots 106c, 5 negative control spots 106c, 6 negative control spots 106c, 7 negative control spots 106c, 8 negative control spots 106c, 9 negative control spots 106c, 10 negative control spots 106c, 11 negative control spots 106c, 12 negative control spots 106c, 13 negative control spots 106c, 14 negative control spots 106c, 15 negative control spots 106c, 16 negative control spots 106c, 17 negative control spots 106c, 18 negative control spots 106c, 19 negative control spots 106c, 20 negative control spots 106c, or more than 20 negative control spots 106c.

In one embodiment microarray 104 is manufactured by printing methods conventionally used for manufacturing high- or low-density microarrays, for example non-contact microarray printing. Other manufacturing methods are also possible including, but not limited to chemical binding of capture agents to microsphere surfaces in solution or in air.

In one embodiment the size of low-density microarray 104 is approximately a 1 cm×1 cm square, and spots 106a-c are each typically circular with a size of approximately 300 micrometers in diameter, patterned in a regularly-spaced rectangular array with center-to-center spacing of approximately 300 micrometers. However, one who is skilled in the art will recognize that many alternative sizes, patterns, shapes and spacings of microarray 104 and spots 106 are possible, both regularly- and irregularly-spaced and rectangular and non-rectangular. For example, the size of microarray 104 may be 0.5 cm×0.5 cm, and spots 106 may be circular with size approximately 100 micrometers in diameter, patterned in an irregularly-spaced circular array. The spacing between spots 106 may also be variable, for example if the spots 106 are distributed over multiple microspheres that are spatially distinct but free to move relative to one another.

In one embodiment, substrate 102 is approximately 25 mm×75 mm in lateral dimensions and 0.5 mm in thickness. However, in other embodiments substrate 102 may be a different size, for example 25 mm×25 mm in lateral dimensions and 0.5 mm in thickness, or 1 cm by 1 cm in lateral dimensions with thickness 1 mm.

In one embodiment, one microarray 104 is printed on substrate 102. However, in other embodiments more than one microarray 104 may be printed on a substrate 102. In other embodiments a microarray 104 may be distributed on multiple substrates 102 so long as spots 106 of microarray 104 are spatially distinct, for example on multiple microspheres.

In one embodiment, spots 106 are grouped into sub-arrays 108 comprising one or more spots 106, each spot 106 targeting the same or different types of antigen, or having the same or different types of capture agents immobilized. In some embodiments, the universal capture array 100 comprises 1 to about 20 sub-arrays 108, for example 1 sub-array, 2 sub-arrays, 3 sub-arrays, 4 sub-arrays, 5 sub-arrays, 6 sub-arrays, 7 sub-arrays, 8 sub-arrays, 9 sub-arrays, 10 sub-arrays, 11 sub-arrays, 12 sub-arrays, 13 sub-arrays, 14 sub-arrays, 15 sub-arrays, 16 sub-arrays, 17 sub-arrays, 18 sub-arrays, 19 sub-arrays, 20 sub-arrays, or more than 20 sub-arrays.

In some embodiments, a sub-array 108 comprises 1 to about 20 spots 106, for example 1 spot, 2 spots, 3 spots, 4 spots, 5 spots, 6 spots, 7 spots, 8 spots, 9 spots, 10 spots, 11 spots. 12 spots, 13 spots, 14 spots, 15 spots, 16 spots, 17 spots, 18 spots, 19 spots, 20 spots, or more than 20 spots. In some embodiments, a sub-array 108 consists of a single type of spot 106, for example a sub-array 108 may consist of one or a plurality of positive control spots 106a, one or a plurality of capture agent spots 106b, or one or a plurality of negative control spots 106c.

In some embodiments, a sub-array 108 consists of a plurality of capture agent spots 106b, wherein each of the plurality of capture agent spots 106c include the same type(s) of capture agent(s). In some embodiments, a sub-array 108 consists of a plurality of capture agent spots 106b, wherein the plurality of capture agent spots 106b include different capture agent(s). In some embodiments, a sub-array 108 consists of a plurality of capture agent spots 106b, wherein the plurality of capture agent spots 106c include the same type(s) of capture agent(s).

In some embodiments, a sub-array 108 includes a plurality of capture agent spots 106b representing a plurality of concentrations of the capture agent(s). For example, in a sub-array 108 a single type of capture agent is printed at different concentrations at different spots 106 in a dilution pattern (e.g., a serial dilution) spanning 0.1 µg/mL to 150 µg/mL to generate a binding curve for quantifying influenza HA. Each concentration in the dilution pattern (e.g., a serial dilution) may be printed one or more times within sub-array 108, for example in triplicate, to improve reliability, repeatability, accuracy, and precision of quantification.

In one embodiment sub-array 108 comprises capture agent spots 106b that include different but related capture agents. For example, capture agents targeting one subset of a class of antigen and a capture agent targeting a different subset of the same class of antigen may be included within a single capture agent spot 106b. For example, an antibody targeting one set of mutations of influenza hemagglutinin subtype 1 and an antibody targeting a different or overlapping set of mutations of influenza hemagglutinin subtype 1 may be printed at capture agent spots 106b that are constituents of the same sub-array 108. In another example, a capture agent targeting a linear epitope of an antigen and a capture agent targeting a conformational epitope of the same or different antigen may be printed at capture agent spots 106b that are constituents of the same sub-array 108. In other embodiments capture agents at capture agent spots 106b of a sub-array 108 are related in different ways.

Sub-array 108 can be configured to target a set of one or more antigens, for example, in the same way that a capture agent can be said to target a set of one or more antigens. The set of antigens targeted by a sub-array 108 is then the same as the set of antigens targeted by capture agents printed at capture agent spots 106b within the sub-array 108. For example, a sub-array 108 comprising capture agent spots 106b including (i) antibodies targeting half of the possible mutations of influenza A HA subtype 1 and (ii) antibodies targeting the other different possible mutations of influenza A HA subtype 1 can be said to itself target all of the possible mutations of influenza A HA subtype 1. As another example, a sub-array 108 comprising capture agent spots 106b including (i) antibodies targeting a conformational epitope of influenza HA from strain A/Victoria/361/2011 and (ii) antibodies targeting a linear epitope of influenza HA from strain A/Victoria/361/2011 are printed can be said to itself target both conformational and linear epitopes of influenza HA from strain A/Victoria/361/2011.

In one embodiment, one sub-array 108 of microarray 104 may target a linear epitope of a protein antigen while a different sub-array 108 of microarray 104 may target a conformational epitope of the same type of protein antigen so as to provide means for quantifying degradation of a protein antigen that does not require a reference sample of the protein antigen at known concentration or a reference sample of the protein antigen that is known to be non-degraded.

In one embodiment, sub-arrays are grouped into sub-array groups comprising one or more sub-arrays 108, each sub-array 108 targeting the same or different types of antigen, or having the same or different types of capture agents immobilized. For example, a sub-array group may target many or all mutations of influenza A hemagglutinin subtype 1.

In one embodiment, the capture agent spots 106b include one or more monoclonal antibodies configured to enable quantification of influenza virus proteins over multiple years despite antigenic drift.

In some embodiments, the capture agent spots 106b include one or more monoclonal antibodies configured to enable simultaneous quantification of multiple influenza virus proteins over several years despite antigenic drift.

In some embodiments, the capture agent spots 106b include a combination of subtype-specific antibodies for influenza A types and lineage-specific antibodies for influenza B configured to enable quantification of specific subtypes or lineages of influenza hemagglutinin.

In some embodiments, the capture agent spots 106b include a combination of subtype-specific antibodies for influenza A types and lineage-specific antibodies for influenza B configured to enable simultaneous quantification of multiple subtypes or lineages of influenza hemagglutinin.

In some embodiments, the capture agent spots 106b include a combination of subtype-specific antibodies and lineage-specific antibodies configured to bind to all influenza A subtypes and influenza B lineages and arranged in an array format to enable quantification of specific subtypes of influenza hemagglutinin.

In some embodiments, the capture agent spots 106b include a combination of subtype-specific antibodies and lineage-specific antibodies configured to bind to a plurality of (e.g., all of) influenza A subtypes and influenza B lineages and arranged in an array format to enable simultaneous quantification of multiple subtypes or lineages of influenza hemagglutinin.

In some embodiments, the capture agent spots 106b include a combination of conformational and linear binding antibodies each capable of binding to one or more of a plurality of predetermined influenza A subtypes and/or influenza B lineages to enable quantification of influenza proteins.

In some embodiments, the capture agent spots 106b include a combination of conformational and linear binding antibodies each capable of binding to one or more of a plurality of predetermined influenza A subtypes and/or influenza B lineages to enable evaluation (e.g., quantification) of influenza protein stability.

In some embodiments, the capture agent spots 106b include a combination of neutralizing and non-neutralizing antibodies each capable of binding to one or more of a plurality of predetermined influenza A types and/or influenza B lineages to enable quantification of influenza proteins.

In some embodiments, the capture agent spots 106b include a combination of neutralizing and non-neutralizing antibodies each capable of binding to one or more of a plurality of predetermined influenza A subtypes and/or influenza B lineages to enable evaluation (e.g., quantification) of protein stability.

In some embodiments, the capture agent spots 106b include a combination of conformational, neutralizing antibodies capable of binding both the variable HA1 region and the conserved HA2 region of influenza hemagglutinin protein to enable quantification of hemagglutinin and evaluation (e.g., quantification) of protein stability.

In some embodiments, the capture agent spots 106b include a combination of conformational, neutralizing antibodies capable of binding both the variable HA1 region and the conserved HA2 region of influenza hemagglutinin protein to enable quantification of hemagglutinin and evaluation (e.g., quantification) of protein stability.

In some embodiments, the capture agent spots 106b include a combination of conformational, neutralizing antibodies capable of binding both the variable HA1 region and the conserved HA2 region of influenza hemagglutinin protein to enable simultaneous quantification of multiple hemagglutinin proteins.

In one embodiment, a universal capture array 100 comprises a micro-array 104 on a substrate 102, the micro-array 104 comprising a positive control spot 106a, a negative control spot 106c, and a first sub-array 103 comprising, consisting of, or consisting essentially of a plurality of capture agent spots 106b each including many or all possible mutations of influenza A HA subtype 1 (A/H1), a second sub-array 108 comprising, consisting of, or consisting essentially of a plurality of capture agents 106b each including many or all possible mutations of influenza A HA subtype 3 (A/H3), a third sub-array 103 comprising, consisting of, or consisting essentially of a plurality of capture agent spots 106b each including many or all possible mutations of Yamagata-lineage influenza B (B/Yamagata) HA, and a fourth sub-array 108 comprising, consisting of, or consisting essentially of many or all possible mutations of Victoria-lineage influenza B (B/Victoria) HA. Such an embodiment is configured to enable multiplexed quantification and subtyping of subcomponents of a single sample (e.g., a quadrivalent vaccine) consisting of any or all mutations of A/H1, any or all mutations of A/H3, any or all mutations of B/Yamagata HA and any or all mutations of B/Victoria that does not require updating of materials or methods each year, in a single test. The first, second, third and fourth set of sub-arrays 108 may each also include one or more sub-arrays 108 comprising, consisting of, or consisting essentially of a plurality of capture array spots 106b configured to bind conformational and linear epitopes of one or more antigens. In such embodiments, the universal capture array 100 is configured to quantify an amount of degradation of one or more subcomponents of a vaccine without the use of a reference sample of the one or more subcomponents at known concentration or a reference sample of the one or more subcomponents that is known to be non-degraded. One who is skilled in the art will recognize that any one or more of the first, second, third and fourth sub-arrays 108, or additional sub-arrays 108 forming a part of universal capture array 100 may bind other sets of one or more antigens not specifically listed above.

In one embodiment, the microarray 104 includes one or more subarrays 108 with capture agent spots 106b configured to bind to hemagglutinin from a pandemic influenza strain. In such embodiments, the capture agent spots 106b may include capture agents comprising an antibody capable of binding hemagglutinin from pandemic or potentially pandemic strains of influenza, including but not limited to influenza A/H1, A/H2, A/H3, A/H5, A/H7, and A/H9.

In one embodiment, the microarray 104 includes nine sub-arrays 108, wherein from 1 to 9 of the sub-arrays 108, for example 1 sub-array 108, 2 sub-arrays 108, 3 sub-arrays 108, 4 sub-arrays 108, 5 sub-arrays 108, 6 sub-arrays 108, 7 sub-arrays 108, 8 sub-arrays 108, or all 9 sub-arrays 108 include an anti-hemagglutinin antibody capable of binding to a hemagglutinin protein in its natural (e.g., not denatured or conformational) configuration. In such an embodiment, the remaining sub-arrays 108, if any, may include an anti-hemagglutinin antibody capable of binding to a hemagglutinin protein in its denatured (e.g., linear) conformation.

In one embodiment, the microarray 104 includes a plurality of sub-arrays 108, wherein at least one of the sub-arrays 108, for example 1 sub-array 108, 2 sub-arrays 108, 3 sub-arrays 108, 4 sub-arrays 108, 5 sub-arrays 108. 6 sub-arrays 108, 7 sub-arrays 108, 8 sub-arrays 108, 9 sub-arrays 108, or more than 9 sub-arrays 108 each include an anti-hemagglutinin antibody capable of binding to a hemagglutinin protein in its natural (e.g., not denatured or conformational) configuration. In such an embodiment, the remaining sub-arrays 108, if any, may include an anti-hemagglutinin antibody capable of binding to a hemagglutinin protein in its denatured (e.g., linear) conformation. In one embodiment, therefore, the microarray 104 may include 6 sub-arrays 108 which each include anti-hemagglutinin antibodies capable of binding to a hemagglutinin protein in its natural (e.g., not denatured or conformational) configuration, and 3 sub-arrays 108 each including anti-hemagglutinin antibodies capable of binding to a denatured (e.g., linear) hemagglutinin protein.

In one embodiment, the microarray 104 includes a plurality of sub-arrays 108, wherein at least one of the sub-arrays 108, for example 1 sub-array 108, 2 sub-arrays 108, 3 sub-arrays 108, 4 sub-arrays 108, 5 sub-arrays 108, 6 sub-arrays 108, 7 sub-arrays 108, 8 sub-arrays 108, 9 sub-arrays 108, or more than 9 sub-arrays 108 each include an anti-hemagglutinin antibody capable of binding to the variable globular head (e.g., HA1) region of a hemagglutinin protein. In such an embodiment, the remaining sub-arrays 108, if any, may include an anti-hemagglutinin antibody capable of binding to the conserved stem region (e.g., HA2 region) of a hemagglutinin protein. In one embodiment, therefore, the microarray 104 may include 7 sub-arrays 108 which each include anti-hemagglutinin antibodies capable of binding to the variable globular head (e.g., HA1) region of a hemagglutinin protein, and two sub-arrays 108 each including anti-hemagglutinin antibodies capable of binding to the conserved stem region (e.g., HA2 region) of a hemagglutinin protein.

In one embodiment, the microarray 104 includes a plurality of sub-arrays 108, wherein at least one of the sub-arrays 108, for example 1 sub-array 108, 2 sub-arrays 108, 3 sub-arrays 108, 4 sub-arrays 108, 5 sub-arrays 108, 6 sub-arrays 108, 7 sub-arrays 108, 8 sub-arrays 108, 9 sub-arrays 108, or more than 9 sub-arrays 108 each include a neutralizing anti-hemagglutinin antibody. In such an embodiment, the remaining sub-arrays 108, if any, may include a non-neutralizing anti-hemagglutinin antibody. In one embodiment, therefore, the microarray 104 may include 5 sub-arrays 108 which each include a neutralizing anti-hemagglutinin antibody, and four sub-arrays 108 each including a non-neutralizing anti-hemagglutinin antibody.

In one embodiment, the microarray 104 includes a plurality of sub-arrays 108, wherein at least one of the sub-arrays 108, for example 1 sub-array 108, 2 sub-arrays 108, 3 sub-arrays 108, 4 sub-arrays 108, 5 sub-arrays 108, 6 sub-arrays 108, 7 sub-arrays 108, 8 sub-arrays 108, 9 sub-arrays 108, or more than 9 sub-arrays 108 each include an anti-hemagglutinin antibody capable of binding broadly to hemagglutinin protein from H1 subtypes of influenza. The microarray 104 may further include at least one sub-array 108, for example 1 sub-array 108, 2 sub-arrays 108, 3 sub-arrays 108, 4 sub-arrays 108, 5 sub-arrays 108, 6 sub-arrays 108, 7 sub-arrays 108, 8 sub-arrays 108, 9 sub-arrays 108, or more than 9 sub-arrays 108, which includes an anti-hemagglutinin antibody capable of binding broadly to hemagglutinin protein from H3 subtypes of influenza. The microarray 104 may further include at least one sub-array 108, for example 1 sub-array 108, 2 sub-arrays 108, 3 sub-arrays 108, 4 sub-arrays 108, 5 sub-arrays 108, 6 sub-arrays 108, 7 sub-arrays 108, 8 sub-arrays 108, 9 sub-arrays 108, or more than 9 sub-arrays 108, which includes an anti-hemagglutinin antibody capable of binding broadly to hemagglutinin protein from influenza B subtypes. The microarray 104 may further include at least one sub-array 108, for example 1 sub-array 108, 2 sub-arrays 108, 3 sub-arrays 108, 4 sub-arrays 108, 5 sub-arrays 108, 6 sub-arrays 108, 7 sub-arrays 108, 8 sub-arrays 108, 9 sub-arrays 108, or more than 9 sub-arrays 108, which includes an anti-hemagglutinin antibody capable of binding specifically to a hemagglutinin protein from a predetermined strain of influenza. In one embodiment, therefore, a microarray 104 may include two sub-arrays 108 including anti-hemagglutinin antibodies capable of binding broadly to hemagglutinin protein from H1 subtypes of influenza, three sub-arrays 108 including anti-hemagglutinin antibodies capable of binding broadly to hemagglutinin protein from H3 subtypes of influenza, three sub-arrays 108 including anti-hemagglutinin antibodies capable of binding broadly to hemagglutinin protein from influenza B subtypes, and one sub-array 108 including anti-hemagglutinin antibodies capable of binding specifically to hemagglutinin protein from a predetermined strain of influenza (e.g., A/CA/2009).

Accordingly, in one embodiment the micro-array 104 includes n sub-arrays 108, wherein: (i) from 0 to n sub-arrays 108 each including an anti-hemagglutinin antibody capable of binding to a hemagglutinin protein in its natural (e.g., not denatured or conformational) configuration, and from n to 0 sub-arrays 108 each including an anti-hemagglutinin antibody capable of binding to a hemagglutinin protein in its denatured (e.g., linear) configuration; (ii) from 0 to n sub-arrays 108 each including an anti-hemagglutinin antibody capable of binding to the variable globular head (e.g., HA1) region of a hemagglutinin protein, and from n to 0 sub-arrays 108 each including an anti-hemagglutinin antibody capable of binding to the conserved stem region (e.g., HA2 region) of a hemagglutinin protein; (iii) from 0 to n sub-arrays 108 each including a neutralizing anti-hemagglutinin antibody, and from n to 0 sub-arrays 108 each including a non-neutralizing anti-hemagglutinin antibody; (iv) from 0 to n sub-arrays 108 each including an anti-hemagglutinin antibody capable of binding broadly to hemagglutinin protein from H1 subtypes of influenza A, from n to 0 sub-arrays 108 each including an anti-hemagglutinin antibody capable of binding broadly to hemagglutinin protein from H3 subtypes of influenza A, from n to 0 sub-arrays 108 each including an anti-hemagglutinin antibody capable of binding broadly to hemagglutinin protein from influenza B, and from n to 0 sub-arrays 108 each including an anti-hemagglutinin antibody capable of binding specifically to hemagglutinin protein from a predetermined strain of influenza.

Accordingly, in one embodiment, the microarray 104 includes 9 sub-arrays 108 (e.g., n is 9) wherein the microarray 104 includes: (i) six sub-arrays 108 each including an anti-hemagglutinin antibody capable of binding to a hemagglutinin protein in its natural (e.g., not denatured or conformational) configuration, and three sub-arrays 108 each including an anti-hemagglutinin antibody capable of binding to a hemagglutinin protein in its denatured (e.g., linear) configuration; (ii) seven sub-arrays 108 each including an anti-hemagglutinin antibody capable of binding to the variable globular head (e.g., HA1) region of a hemagglutinin protein, and two sub-arrays 108 each including an anti-hemagglutinin antibody capable of binding to the conserved stem region (e.g., HA2 region) of a hemagglutinin protein; (iii) five sub-arrays 108 each including a neutralizing anti-hemagglutinin antibody, and four sub-arrays 108 each including a non-neutralizing anti-hemagglutinin antibody; (iv) two sub-arrays 108 each including an anti-hemagglutinin antibody capable of binding broadly to hemagglutinin protein from H1 subtypes of influenza, three sub-arrays 108 each including an anti-hemagglutinin antibody capable of binding broadly to hemagglutinin protein from H3 subtypes of influenza, three sub-arrays 108 each including an anti-hemagglutinin antibody capable of binding broadly to hemagglutinin protein from influenza 8, and one sub-array 108 including an anti-hemagglutinin antibody capable of binding specifically to hemagglutinin protein from a predetermined strain of influenza.

Accordingly, in one embodiment, the microarray 104 include 9 sub-arrays 108 (e.g., n is 9), wherein: (i) one sub-array 108 including a neutralizing anti-hemagglutinin antibody capable of binding to a hemagglutinin protein in its natural (e.g., not denatured or conformational) configuration, a variable (e.g., HA1) region of a specific strain of influenza hemagglutinin; (ii) one sub-array 108 including a neutralizing broad anti-H1 antibody capable of binding to a hemagglutinin protein in its natural (e.g., not denatured or conformational) configuration at a conserved (e.g., HA2) region of an influenza hemagglutinin protein; (iii) one sub-array 108 including a non-neutralizing broad anti-H1 antibody capable of binding to a hemagglutinin protein in its denatured (e.g., linear) configuration of a variable (e.g., HA1) region of an influenza hemagglutinin protein; (iv) one sub-array 108 including a neutralizing broad anti-H3 antibody capable of binding to a hemagglutinin protein in its natural (e.g., not denatured or conformational) configuration at a variable (e.g., HA1) region of an influenza hemagglutinin protein; (v) one sub-array 108 including a non-neutralizing broad anti-H3 antibody capable of binding to a hemagglutinin protein in its natural (e.g., not denatured or conformational) configuration at a conserved (e.g., HA2) region of an influenza hemagglutinin protein; (vi) one sub-array 108 including a non-neutralizing broad anti-H3 antibody capable of binding to a hemagglutinin protein in its denatured (e.g., linear) configuration of a variable (e.g., HA1) region of an influenza hemagglutinin protein; (vii) two sub-arrays 108 each including a neutralizing broad anti-influenza B antibody capable of binding to a hemagglutinin protein in its natural (e.g., not denatured or conformational) configuration at a variable (e.g., HA1) region of an influenza hemagglutinin protein; and (viii) one sub-array 108 including a non-neutralizing broad anti-influenza B antibody capable of binding to a hemagglutinin protein in its denatured (e.g., linear) configuration of a variable (e.g., HA1) region of an influenza hemagglutinin protein. In some embodiments, one of the two sub-arrays 108 including a neutralizing broad anti-influenza B antibody capable of binding to a hemagglutinin protein in its natural (e.g., not denatured or conformational) configuration at a variable (e.g., HA1) region of an influenza hemagglutinin protein broadly binds to influenza B from one lineage (e.g., the B/Yamagata lineage), while the other of the two sub-arrays 108 broadly binds to influenza B from a second, different lineage (e.g., the B/Victoria lineage).

In some embodiments, the capture agents are selected from the group consisting of: anti-HA CM3S3 (e.g., CR1-M2S3, Acro), anti-A (e.g., MA1-10512, Pierce), anti-A/pdmH1N1 (e.g., FR-572, ATCC), anti-HA seasonal (e.g., 003-001M13, ImmuneTech), anti-H1 (e.g., C01278M, C01281M, C01282M and/or C86304M, Meridian), anti-H1 seasonal (e.g., 003-001M20, 003-001M21, ImmuneTech), anti-H1 universal (e.g., 003-001M26, ImmuneTech), anti-H1 California (e.g., NR19864, NR19866 and/or NR 19867, BEI Resources; 003-001M4, ImmuneTech), anti-HA California (e.g., 003-001M5, ImmuneTech), anti-H1/Brisbane/59/007 (e.g., 003-007M9, ImmuneTech), anti-H1/H2 (e.g., M145, Clontech), anti-H3 (e.g., FR-54, ATCC; M146, Clontech; C01318M and/or C01319M, Meridian), anti-H3 universal mAb (e.g., 003-00423M4, ImmuneTech), anti-H3 universal (e.g., 003-00423M10, ImmuneTech), anti-H3 seasonal (e.g., 003-004M2, ImmuneTech), anti-H3/Victoria3612011 (e.g., 003-00423M3, ImmuneTech), anti-H3/Brisbane/10/2007 (e.g., 003-004M1, ImmuneTech), anti-H3 Perth (e.g., 003-004M13 and/or 003-004M15, ImmuneTech), anti-HA B/Wisc, Bris, Maly (e.g., 003-032M6, ImmuneTech), anti-HA B Yamanashi (e.g., 003-810M1, ImmuneTech), anti-H5/Vietnam/2011 (e.g., 003-00523M8, ImmuneTech), anti-H5/indonesia2005 (e.g., 003-005lM1, ImmuneTech), anti-H5 Neth 2003 (e.g., C01609M, Meridian), anti-H5 Mab PAN (e.g., 003-05M19 and/or 003-05M22, ImmuneTech), anti-H7 (e.g., 003-008M1, ImmuneTech), anti-H7/Netherlands (e.g., 003-008M8, ImmuneTech), anti-H14 (e.g., 003-017M2, ImmuneTech), anti-B (e.g., 003-B9M1 and/or 003-B9M2, immuneTech, and/or FR-1218, ATCC), anti-B/Brisbane 2008 (e.g., 003-032M2, ImmuneTech), anti-B-Brisbane60/2008 (e.g., 003-032M3, ImmuneTech), anti-B/Wisc (e.g., 003-032M7 and/or 003-032M9, ImmuneTech), anti-B/Wisc 2012 (e.g., 003-B8M1 and/or 003-B8M3, ImmuneTech), and anti-B Texas Pan to B (e.g., 003-B12M3, ImmuneTech).

FIGS. 2A-2B illustrate the operation of one embodiment of a universal capture array 100. In FIG. 2A, capture agent 200 printed at a spot 106b on substrate 102 is contacted with one or more antigens 202 at unknown concentration. Capture agent 200 has binding affinity for antigen 202, which binds to form bound complex 203. In one embodiment, antigen 202 is bound by capture agent 200 when antigen 202 is in its native state in solution, not when it is immobilized directly onto a solid support, meaning antigen 202 is not denatured by the method in such a way that might adversely affect the outcomes of the method.

A signal that correlates with the amount of bound complex 203 at each spot 106 is then generated and quantified using methods suitable for use with low-density microarrays. In one embodiment, a fluorescence-based immunosandwich-type assay is used to generate a fluorescence signal at each spot 106 that correlates with the amount of bound complex 203 at each spot 106b. In such embodiments, a commercially available microarray scanner or similar device may be used to quantify the fluorescent signal at each spot 106. Preferably, the method used to generate a signal requires only a single primary labeling step for all of the bound complexes 203 at all spots 106b comprising various antigens captured on the microarray 104. For example, bound complexes 203 may be labeled in a single step with a mixture or cocktail of broadly cross-reactive biotinylated (209) primary label antibodies 204 that are themselves subsequently labeled with secondary label 206, such as streptavidin, conjugated to signal-generating reporter label 208, for example Cy3 dye, which generates a fluorescent signal that is quantified using a GenePix 4100 microarray scanner from Molecular Devices. However, many other methods for quantifying bound complex 203 on a low-density microarray are suitable for use with the technology, as will be recognized by a person having ordinary skill in the art.

In another embodiment, a signal that correlates with the amount of bound complex 203 at a spot 106b is generated by labeling antigen 202 with a label to form a labeled antigen 203a prior to contacting with the microarray 104. For example, antigen 202 may be biotinylated (209) and labeled with a secondary label 206 (e.g., streptavidin) conjugated to a signal-generating reporter label 208 to generate labeled antigen complex 203a. After exposing microarray 104 to the labeled antigen 203a, a microarray scanner or similar device may subsequently be used to quantify the fluorescent signal at a spot 106a-c of the microarray 104.

In another embodiment, a signal that correlates with the amount of bound complex 203 at a spot 106b is generated by contacting microarray 104 with an antibody that has affinity to bind antigen 202 or bound complex 203 and that is conjugated directly to a signal-generating reporter label 208. For example, an antibody with binding affinity for antigen 202 and that is directly conjugated to a signal-generating reporter label 208 may be contacted to the microarray 104, and a GenePix 4100 microarray scanner from Molecular Devices or a similar device may be used to quantify the fluorescence at a spot 106a-c.

In another embodiment, a signal that correlates with the amount of bound complex 203 at a spot 106a-c is generated by directly conjugating bound complex 203 with a signal-generating reporter label 208. For example, a fluorescent dye that stains bound complex 203 but not capture agent 200 alone may be used as a signal-generating reporter label 208 to label bound complex 203 and a GenePix 4100 microarray scanner from Molecular Devices or a similar device may subsequently be used to quantify the fluorescence at a spot 106a-c.

In one embodiment one or more calibration curves are constructed using one or more arrays 104 and one or more antigens 202 at known reference concentrations. One or more reference antigens 202 at known concentrations are contacted with one or more arrays 104, and a signal that correlates with the amount of bound complex 203 at capture array spots 106b is generated and quantified using appropriate methods suitable for use with low-density microarrays as previously described to form one or more calibration curves that yield a relationship between quantity of fluorescence signal at capture array spots 106b and absolute initial concentration of one or more antigens 202. In one embodiment, 6 different concentrations of a serially-diluted sample containing one or more types of influenza hemagglutinin (e.g., a trivalent vaccine, a quadrivalent vaccine, or any one or more component thereof) in which the concentration of each component of the sample is known may be contacted with 6 different arrays 104 or sub-arrays 108 to form bound complexes 203, that are then labeled with a cocktail of biotinylated antibodies 204, and subsequently labeled with a secondary label (e.g., streptavidin) conjugated to a signal-generating reporter label 208 (e.g., Cy3 fluorescent dye), and the fluorescent signal at capture array spots 106b may be quantified using a GenePix 4100 microarray scanner from Molecular Devices or a similar device to form calibration curves that yield a relationship between quantity of fluorescence signal at capture array spots 106b and initial absolute concentration of each of the components of the vaccine.

In another embodiment, a series (e.g., 2-6) of single antigen samples having known antigen concentrations may be contacted with a series (e.g., 2-6) of different microarrays 104 or sub-arrays 108 to form bound complexes 203, that are then labeled with a biotinylated antibody 204, and subsequently labeled with a secondary label (e.g., streptavidin) conjugated to a signal-generating reporter label 208 (e.g., Cy3 fluorescent dye), and the fluorescent signal at capture array spots 106b may be quantified using the methods described above.

In one embodiment, calibration curves are obtained after immobilization of capture agents 200, which are localized at known concentration in capture array spots 106b. In this embodiment, the method comprises contacting array 104 with antigen 202 having unknown concentration and subsequently determining a relationship between one or more quantities of fluorescence signal at spots 106a-c and absolute initial concentration of one or more antigens 202 provided by one or more calibration curves. Accordingly, this embodiment inherently accounts for any denaturation of capture agents 200 that may occur as a result of localization of capture agents 200 in capture array spots 106b.

In one embodiment, the method that is used to generate and quantify a signal from bound complex 203 after contacting with one or more antigens 202 at known reference concentrations is the same as the method used to generate and quantify a signal from bound complex 203 after contacting microarray 104 with one or more antigens 202 at one or more unknown concentrations.

In one embodiment, the quantified signal at one or more capture array spots 106b on microarray 104 is used to determine an unknown absolute concentration of antigen 202 by comparison to a calibration curve. For example, an amount of fluorescent signal generated by an unknown initial concentration of an antigen 202 may be compared to one or more fluorescent signals that comprise a portion of a calibration curve generated with the same antigen 202 at one or more known initial concentrations to determine the unknown initial concentration.

In one embodiment, signals from one or more capture array spots 106b on microarray 104 are compared to signals from a different one or more capture array spots 106b on microarray 104 in order to measure the fraction of degraded protein in a vaccine. For example, the amount of signal generated at a first capture array spot 106b with capture agent 200 printed at a concentration and targeting a conformational epitope of an antigen 202 may be compared to the amount of signal generated at a second capture array spot 106b with capture agent 200 printed at the same concentration targeting a linear epitope of an antigen 202 to yield the relative amount of antigen 202 that is denatured, according to equation (1):

$$R = \frac{S_l/K_{a,l}}{S_c/K_{a,c}} \quad (1)$$

where R is the ratio of the amount of antigen 202 that is denatured to the amount of antigen 202 is that non-degraded, $S_1$ and $S_c$ are the quantified signals generated at first and second capture array spots 106b targeting a linear epitope and a conformational epitope of an antigen 202 respectively, and $K_{a,l}$ and $K_{a,c}$ are the association constants for the linear epitope- and conformational epitope-binding reactions, respectively.

In one embodiment, an unknown absolute concentration of degraded protein antigen 202 in a sample is measured by calculating R in equation (1) and multiplying it by an absolute concentration of non-degraded protein antigen 202 obtained by comparing the quantified signal from one or more capture array spots 106b on microarray 104 to calibration curves as described herein.

Figure 4:
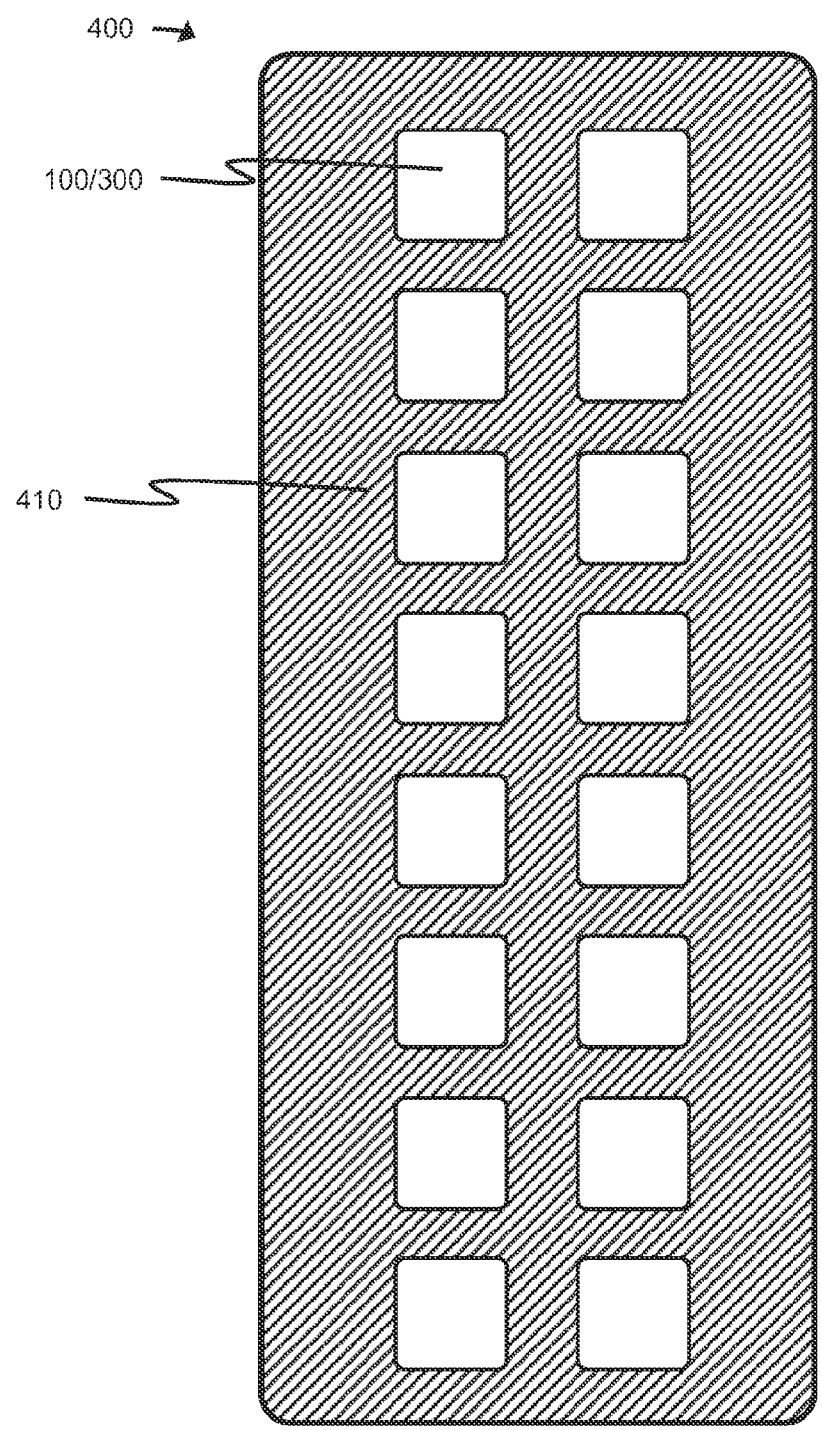
FIG. 4 shows one embodiment of a chip including a plurality of microarrays consistent with the present disclosure.

Referring now to FIG. 4, multiple microarrays 100/300 can be arranged on a single substrate to provide a chip 400. Chip 400 may include as many microarrays 100/300 that can be arranged in a non-overlapping configuration on one surface of the chip 400. Although the chip 400 illustrated in FIG. 4 includes 16 microarrays 100/300, chip 400 may include fewer than 16 microarrays 100/300, or more than 16 microarrays 100/300. In some embodiments, the chip 400 includes multiple microarrays 100/300, wherein each of the microarrays 100/300 are identical (e.g., each microarray 100/300 includes the same configuration of spots 106a-c with the same capture agent(s) at each spot 106a-c). In other embodiments, the chip 400 includes microarrays 100/300 with different configurations (e.g., different arrangement of spots 106a-c, different number of spots 106a-c, and/or different capture agent(s) at spots 106a-c).

In some embodiments, the chip 400 includes from 1 to about 100 microarrays, for example 1 microarray, 2 microarrays 100/300, 3 microarrays 100/300, 4 microarrays 100/300, 5 microarrays 100/300. 6 microarrays 100/300, 7 microarrays 100/300, 8 microarrays 100/300, 9 microarrays 100/300, 10 microarrays 100/300, 11 microarrays 100/300, 12 microarrays 100/300, 13 microarrays 100/300. 14 microarrays 100/300, 15 microarrays 100/300, 16 microarrays 100/300, 17 microarrays 100/300, 18 microarrays 100/300, 19 microarrays 100/300, 20 microarrays 100/300. 21 microarrays 100/300, 22 microarrays 100/300, 23 microarrays 100/300, 24 microarrays 100/300, 25 microarrays 100/300, 26 microarrays 100/300, 27 microarrays 100/300. 28 microarrays 100/300, 29 microarrays 100/300, 30 microarrays 100/300, 31 microarrays 100/300, 32 microarrays 100/300, 33 microarrays 100/300, 34 microarrays 100/300, 35 microarrays 100/300, 36 microarrays 100/300, 37 microarrays 100/300, 38 microarrays 100/300, 39 microarrays 100/300, 40 microarrays 100/300, 41 microarrays 100/300. 42 microarrays 100/300, 43 microarrays 100/300, 44 microarrays 100/300, 45 microarrays 100/300, 46 microarrays 100/300, 47 microarrays 100/300, 48 microarrays 100/300, 49 microarrays 100/300, 50 microarrays 100/300, 51 microarrays 100/300, 52 microarrays 100/300, 53 microarrays 100/300, 54 microarrays 100/300, 55 microarrays 100/300, 56 microarrays 100/300, 57 microarrays 100/300. 58 microarrays 100/300, 59 microarrays 100/300, 60 microarrays 100/300, 61 microarrays 100/300, 62 microarrays 100/300, 63 microarrays 100/300, 64 microarrays 100/300, 65 microarrays 100/300, 66 microarrays 100/300, 67 microarrays 100/300, 68 microarrays 100/300, 69 microarrays 100/300, 70 microarrays 100/300, 71 microarrays 100/300. 72 microarrays 100/300, 73 microarrays 100/300, 74 microarrays 100/300, 75 microarrays 100/300, 76 microarrays 100/300, 77 microarrays 100/300, 78 microarrays 100/300, 79 microarrays 100/300, 80 microarrays 100/300, 81 microarrays 100/300, 82 microarrays 100/300, 83 microarrays 100/300, 84 microarrays 100/300, 85 microarrays 100/300, 86 microarrays 100/300, 87 microarrays 100/300. 88 microarrays 100/300, 89 microarrays 100/300, 90 microarrays 100/300, 91 microarrays 100/300, 92 microarrays 100/300. 93 microarrays 100/300, 94 microarrays 100/300, 95 microarrays 100/300, 96 microarrays 100/300, 97 microarrays 100/300, 98 microarrays 100/300, 99 microarrays 100/300, or 100 microarrays 100/300. In some embodiments the chip 400 includes more than 100 microarrays 100/300.

The chip 400 may further include a mask 410. In some embodiments, the mask 410 provides a visual indicator of where the multiple microarrays 100/300 are located on the chip 400. In some embodiments, the mask 410 provides a fluid barrier that confines a predetermined amount of a sample fluid (e.g., about 50 μL) within an area corresponding to one microarray 100/300.

In some embodiments, the chip 400 is configured to fit in a fluorescent slide reader, such as GenePix 4100 (Molecular Devices) or Vidia (InDevR Inc.). For example, the chip 400 may have dimensions of approximately 7.6 cm long (3 inches) by 2.5 cm (1 inch) wide by 1 mm thick. One skilled in the art will readily recognize that other dimensions of the chip 400 are possible such that the chip 400 is configured to fit in and operate with a fluorescent signal detector. For example and without limitation, the chip 400 may have dimensions similar to that of a standard multi-well plate, for example a 6-well plate, a 12-well plate, a 24-well plate, a 48-well plate, or a 96-well plate.

In some embodiments, a chip 400 has dimensions similar to that of a standard 6-well plate, such as a length of about 127-128 mm, a width of about 85-86 mm, and a thickness of about 19-20 mm. The chip 400 may include any suitable number of microarrays 100/300, for example 6 microarrays 100/300, optionally arranged in a pattern of 2 rows and 3 columns, and each microarray 100/300 configured to retain about 16.8 mL of fluid.

In other embodiments, a chip 400 has dimensions similar to that of a standard 12-well plate, such as a length of about 127-128 mm, a width of about 85-86 mm, and a thickness of about 19-20 mm. The chip 400 may include any suitable number of microarrays 100/300, for example 12 microarrays 100/300, optionally arranged in a pattern of 3 rows and 4 columns, and each microarray 100/300 configured to retain about 6.9 mL of fluid.

In other embodiments, a chip 400 has dimensions similar to that of a standard 24-well plate, such as a length of about 127-128 mm, a width of about 85-86 mm, and a thickness of about 19-20 mm. The chip 400 may include any suitable number of microarrays 100/300, for example 24 microarrays 100/300, optionally arranged in a pattern of 4 rows and 6 columns, and each microarray 100/300 configured to retain about 1.8 mL, about 1.9 mL, about 2.4 mL, or about 3.2 mL of fluid.

In other embodiments, a chip 400 has dimensions similar to that of a standard 48-well plate, such as a length of about 127-128 mm, a width of about 85-86 mm, and a thickness of about 19-20 mm. The chip 400 may include any suitable number of microarrays 100/300, for example 48 microarrays 100/300, optionally arranged in a pattern of 6 rows and 8 columns, and each microarray 100/300 configured to retain about 0.95 mL of fluid.

In other embodiments, a chip 400 has dimensions similar to that of a standard 96-well plate, such as a length of about 127-128 mm, a width of about 85-86 mm, and a thickness of about 14-16 mm. The chip 400 may include any suitable number of microarrays 100/300, for example 96 microarrays 100/300, optionally arranged in a pattern of 3 rows and 12 columns, and each microarray 100/300 configured to retain about 100 µL of fluid, about 350 µL of fluid, about 360 µL of fluid, or about 400 µL of fluid.

In one embodiment, a chip 400 includes 96 microarrays 100/300 arranged in a pattern of 3 rows and 12 columns. Each microarray 100/300 may be configured to retain about 50 µL to about 500 µL of sample fluid or reference sample fluid, for example 50 µL, 100 µL, 150 µL, 200 µL, 250 µL, 300 µL, 350 µL, 400 µL, 450 µL, or 500 µL. In one embodiment, the chip 400 includes 96 microarrays 100/300 in an 8×12 pattern and an overall dimension of about 85-86 mm wide by 127.4-127.8 mm long by 14.6-14.7 mm high.

In operation, a chip 400 including multiple microarrays 100/300 can be used to simultaneously generate a calibration curve, quantify influenza proteins, and determine the stability of influenza proteins. In such an embodiment, each of a first portion of the microarrays 100/300 on the chip 400 is contacted with different concentrations of one or more reference hemagglutinin standards. Each of the remaining microarrays 100/300 on the chip 400 is contacted with an unknown concentration of one or more influenza hemagglutinin proteins. After exposure to fluorescent labels as described herein, the chip 400 is analyzed using a fluorescent slide reader (e.g., GeneFix 4100, Molecular Devices; Vidia, lnDevR Inc.) which has been configured to:

1) analyze the first portion of the microarrays 100/300 for generating a calibration curve as a function of the fluorescence intensity of the capture agent spots 106b/306b and the known reference hemagglutinin concentrations, and optionally further as a function of the fluorescence intensities of the positive control spots 106a/306a and/or the negative control spots 106c; and
2) analyze the remaining microarrays 100/300 to determine the concentration(s) of hemagglutinin protein(s) as a function of the fluorescence intensities of the capture agent spots 106b/306b and the calibration curve data, and optionally further as a function of the fluorescence intensities of the positive control spots 106a/306a and/or the negative control spots 106c.

In one embodiment, multiple universal capture arrays 100 that have the same printed capture agents 200 are used to quantify, subtype, and measure degradation of all of the subcomponents of one or more multivalent influenza vaccines comprising one or more protein antigens 202.

In any embodiment described herein, a method of quantifying influenza protein antigens 202 may include subtracting a background noise level (e.g., a background fluorescence level) from a raw fluorescence measurement. Alternatively or in addition to the above, any embodiment described herein may include subtracting a mean or median background noise level (e.g., a mean or median background fluorescence level) from a mean or median raw fluorescence measurement.

In any embodiment described herein, a method of quantifying influenza protein antigens 202 may include normalizing a raw fluorescence measurement, for example by reference to an internal fluorescence standard measurement. Alternatively or in addition to the above, any embodiment described herein may include normalizing a mean or median raw fluorescence measurement for example by reference to a mean or median internal fluorescence standard measurement.

In any embodiment described herein, a method of quantifying influenza protein antigens 202 may include normalizing a raw fluorescence measurement by reference to an internal fluorescence standard measurement after first subtracting a background noise level (e.g., a background fluorescence level) from the raw fluorescence measurement and the internal fluorescence standard measurement. Alternatively or in addition to the above, any embodiment described herein may include normalizing a mean or median raw fluorescence measurement by reference to a mean or median internal fluorescence standard measurement after first subtracting a mean or median background noise level (e.g., a mean or median background fluorescence level) from the mean or median raw fluorescence measurement and the mean or median internal fluorescence standard measurement.

EXAMPLES

Example 1

Antibody Screening for "Universal" Panel. To arrive at a universal capture array in accordance with the described invention, a wide range of commercially available antibodies, including purified monoclonals, polyclonals, and antisera were evaluated. More than 200 antibodies were screened for subtype specificity (ideal as capture antibodies) and broad reactivity (ideal for detection). Antibodies were diluted into spotting buffer (Nexterion Spot PB, Schott Inc.) at a range of concentrations and each concentration spotted onto epoxy-coated glass slides (Nexterion Slide E, Schott; Applied Microarrays Inc.). Performance was evaluated by quantifying the response to subtype-specific HA antigens. Criteria for capture antibodies to be included in the panel included a reasonable binding affinity (as determined by a limit of detection below 0.5 µg/mL), low cross-reactivity with antigens of other subtypes, and commercial availability. Influenza antigens were obtained from Protein Sciences Corporation, BEI Resources, and the Center for Biologics Evaluation and Research (CBER). Archived vaccines obtained from BEI Resources had a variety of matrices such as PBS and PBS with 0.05% gelatin, with and without 0.01% thimerosal.

Monoclonal IgGs (mAbs, mouse) were used as capture antibodies. Subtype specific antisera were screened as capture agents but not utilized further as they exhibited prohibitively elevated backgrounds on the microarray. In general, polyclonal antibodies exhibited unacceptable levels of cross-reactivity and were not used as capture agents. Both conformational and linear antibodies mAbs were evaluated, and a mix of conformational and linear antibodies was selected for influenza A/H1, A/H3 and B. A combination of conformational and neutralizing mAbs against both HA1 and the highly conserved region of HA2 were also selected. At least one linear antibody is included for H1 and H3 subtypes in order to provide additional and complementary insight into protein structure.

Figure 3A:
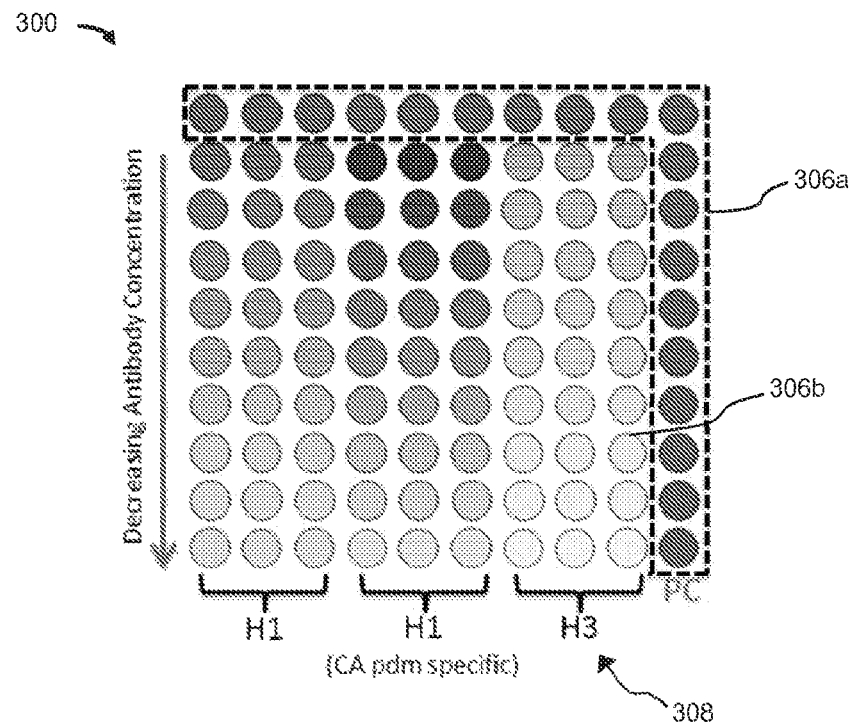
FIGS. 3A-3B show a schematic illustration of an arrangement of molecular captures and fluorescence signals generated at spots of universal capture arrays used to quantify influenza HA according to one embodiment of the present disclosure.

Assay Protocol. As shown in FIG. 3A, a simple microarray 300 was prepared including a series of positive control spots 306a and three subarrays 308, each subarray 308 including a different monoclonal capture antibody. One subarray 308 included spots 306b each including a first capture agent configured to bind to H1; a second subarray 308 included spots 306b each including a second, different capture agent configured to bind to H1. A third subarray 308 included spots 306b each including a capture agent configured to bind to H3. The spots 306a within each subarray 308 included three spots per capture agent concentration. Each subarray 308 included a variety of capture agent concentrations which, in this example, were organized in decreasing concentration as shown by the arrow to the left of the microarray 300. Experimental variables included protein spotting concentrations and conditions, microarray pre-use handling (e.g., washing and blocking), antigen binding time and buffer conditions, label antibody concentration and binding time, and post-labeling wash buffer and conditions.

An appropriate volume (always<10 µL) of the antigen was diluted into blocking buffer (ToC-5531, InDevR Inc.) to yield a minimum of 60 µL. The resulting solution was placed directly onto an array that had been pre-washed in wash buffer 1 (ToC-5532, InDevR Inc.) for 5 minutes on an orbital shaker set at 50 RPM. The array was incubated in a humidity chamber at room temperature for one hour. Excess material was removed by pipette and the slides washed in wash buffer 1 for 1 minute and wash buffer 2 (ToC-5533, InDevR Inc.) for 5 minutes, both at 50 RPM. After removal of excess wash solution, the appropriate subtype specific label (ToC-5512-15, InDevR Inc.) was added and incubated at room temperature for 30 minutes. Excess label was removed and the slide was washed with wash buffers 1 and 2 as previously described. Excess liquid was removed prior to imaging on a fluorescence microarray scanner (either GenePix 4100, Molecular Devices or Vidia, InDevR Inc.), Quantitative data was extracted using manufacturer's software and results were processed using an automated algorithm. Forty microarrays (assays) can be processed in 2-3 hours with this method.

Quantification Algorithm. Given the substantial amount of information obtained from a single microarray, data handling is a critical step in the assay. An algorithm was developed to enable automated analysis of all data from each image as well as automated concentration determination of an unknown using calibration curves. The image analysis algorithm automatically: i) extracts the digital signal from each spot in the image, ii) normalizes the analyte signal to the internal positive control signal, iii) analyzes a matrix of fluorescence signal, spotted antibody concentration, and HA concentration, iv) determines linear response ranges for each spotted antibody concentration when plotted against standard HA concentration (linearity is defined by 4 adjacent points that yield a Pearson's correlation coefficient ($R^2$>0.95) when fit with a linear regression), and v) uses the linear regression fit to back-calculate concentrations for samples of unknown concentration using all of the calibration data in which the fluorescent signal falls within a linear range.

Normalization of the signal on each array using an internal control is used to account for array-to-array variability during manufacture or processing. The internal control is a goat protein capture agent that is subsequently labeled with a fluor-tagged mouse anti-goat IgG during the labeling step. The average value from each triplicate spot is divided by the average value from all internal control spots (N>10) and the result multiplied by 100 to adjust for scale. Background averages and standard deviation are obtained from the space between positive control spots. The background values were used to determine the lower limit of detection and quantification.

Figure 2:
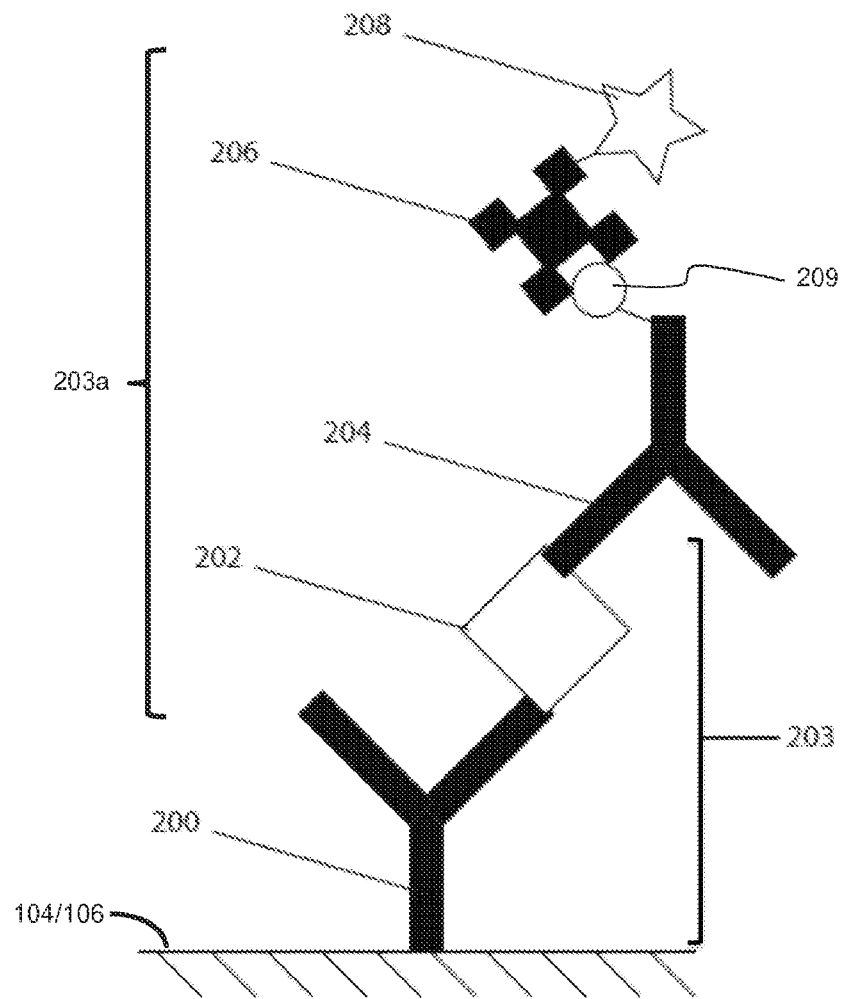
FIG. 2 shows a schematic illustration of operation of a universal capture array according to one embodiment of the present disclosure.
Figure 3B:
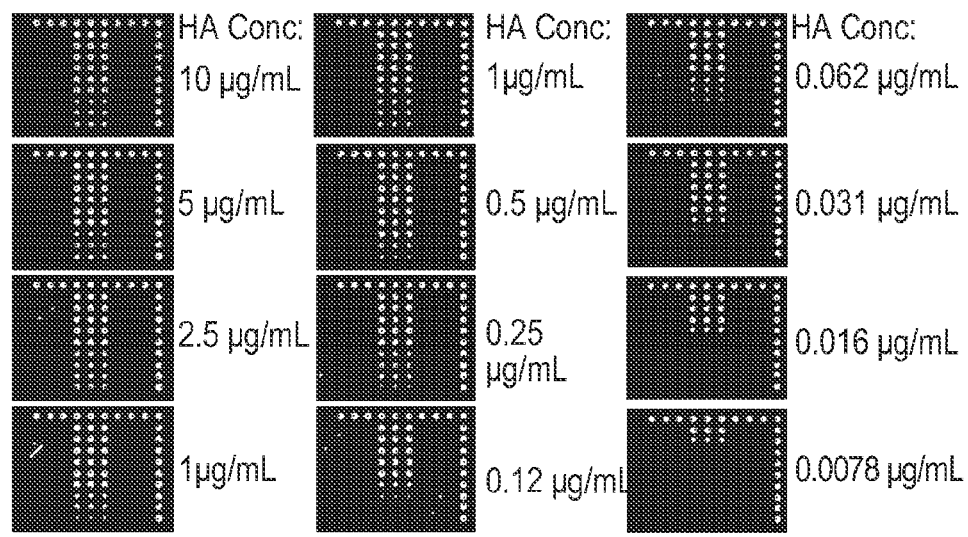

As shown schematically in FIG. 2, influenza subtype-specific monoclonal antibodies (mouse, IgG) immobilized on an epoxy-coated glass slide were used to capture influenza HA. As in a standard sandwich assay, captured HA antigen was subsequently labeled with biotinylated antibody and Cy3-conjugated streptavidin (or alternatively labeled with a fluor-conjugated antibody). Each capture antibody was printed in triplicate in ~200 µm diameter spots at 8 concentrations (2× serial dilutions), as graphically shown in FIG. 3A. Internal positive controls were also printed along the borders of the array for use in signal normalization. Example fluorescence images for recombinant HA from A/CA/H1N1(pdm) (Protein Sciences Corp., Meriden, Conn.) at a variety of concentrations are shown in FIG. 3B. Note that the highest spotted concentrations yield the highest fluorescence signals.

Figure 5A:
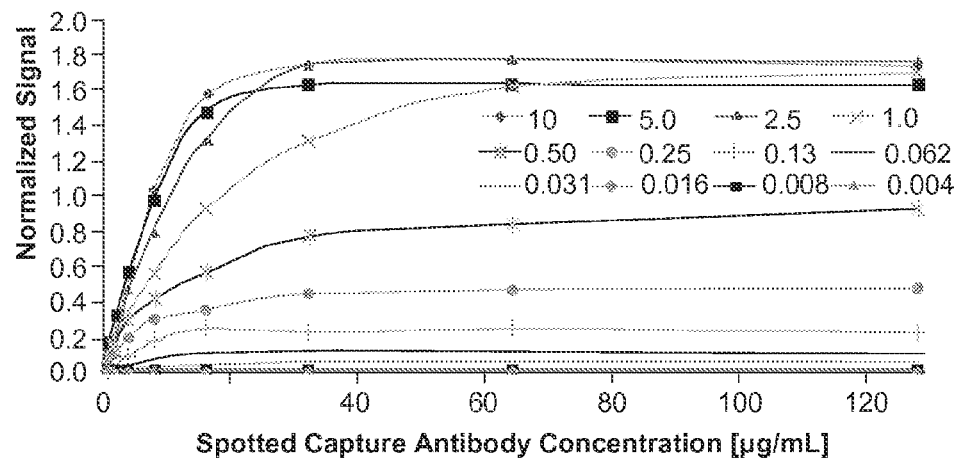
FIGS. 5A-5B show graphs of normalized fluorescence signals versus capture concentration for a variety of target antigen concentrations and a calibration curve according to one embodiment of the present disclosure.

In traditional ELISAs, binding curves are obtained by varying the antigen concentration within a 96 well plate coated with a fixed capture antibody concentration. In one embodiment of the current invention, multiple concentrations of capture antibody within each "well" enable generation of a complete binding curve with a single antigen concentration, as shown in FIG. 5A. The advantage of this approach is more efficient identification of the optimal concentrations for extracting quantitative information. For example, at high antigen concentrations the highest capture antibody concentrations are saturated (see 10 µg/mL HA in FIG. 3B) and cannot be used to quantify. In those cases, lower capture antibody concentrations do yield quantitative information. Likewise, at very low antigen concentrations (see 0.0078 µg/mL HA in FIG. 3B) only the highest capture antibody concentrations provide quantitative information.

Figure 5B:
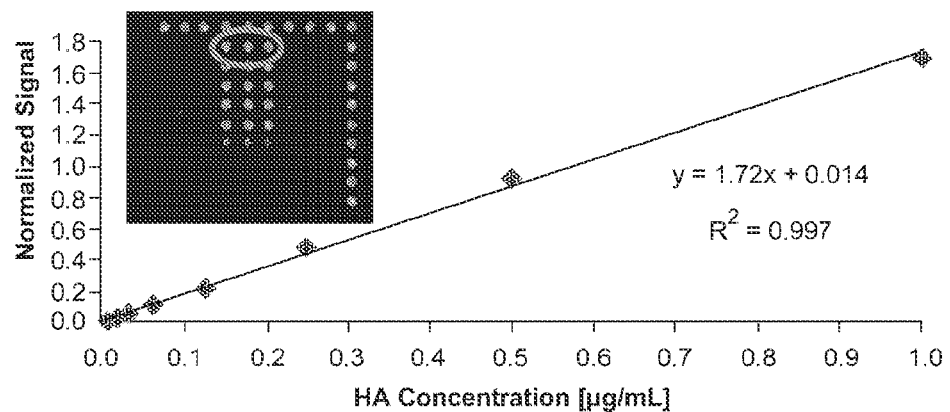

Analytical Sensitivity. For calibration of the microarray, the response to a range of antigen concentrations is mapped out for every antibody concentration resulting in a multi-parametric dataset that can be used to extract quantitative information with greater precision than a single SRID or ELISA measurement. Since each antibody concentration printed in the array will exhibit a slightly different linear range, an automated algorithm was devised to identify and fit the linear range of each calibration curve. Within the algorithm, linearity is defined by a minimum 4 consecutive points that yield a Pearson's correlation of >0.95. An example linear calibration curve for the highest antibody concentration (~100 µg/mL) is shown in FIG. 5B, The linear range is (~1-0.008 µg/mL HA antigen), which is consistent with typical reported ranges for ELISA. The lower limit of detection (<0.008 µg/mL for A/CA/H1) is orders of magnitude better than for SRID, which is limited to concentrations above 3-5 µg/mL. When an "unknown" antigen is analyzed, the automated algorithm compares the measured normalized signal at each antibody concentration to the corresponding calibrated response for that antibody. If the measured response is within a linear region of the binding curve, the linear regression equation for the calibration standards is used to back-calculate the antigen concentration. Since each antibody concentration is spotted in triplicate and multiple antibody concentrations can be used to back-calculate a given antigen concentration, each microarray test can yield multiple measurements thereby providing a high level of precision. While the quantification range of both ELISA and the microarray is lower than SRID, serial dilutions are used in most FDA-approved protocols for HA quantification and should not present a significant problem for achieving acceptable accuracy and precision using the microarray.

The reference recombinant antigens were calibrated against the gold standard method of SRID and used as a secondary standard in this study; thus, the concentrations back-calculated from the calibration curves are calibrated SRID values.

Figure 6:
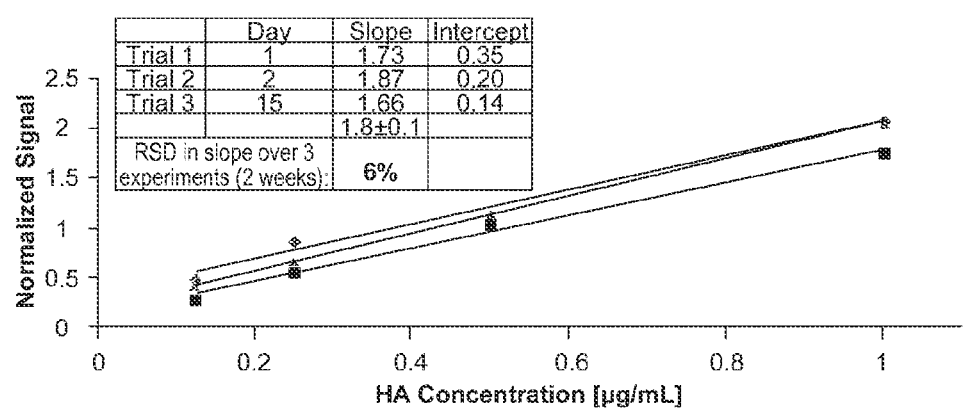
FIG. 6 shows an evaluation of reproducibility of calibration curves according to one embodiment of the present disclosure.

The reproducibility of the calibrated response on the microarray shown in FIG. 3A was evaluated with three samples over a two week time period. FIG. 6 shows data and linear regressions to HA concentrations quantified with the highest (~100 μg/mL) capture antibody spotted concentration over the time period. This data demonstrates good reproducibility, with a relative standard deviation in the slope of 6%.

Example 2

The specificity of the universal array response was determined in order to evaluate reliability for multiplex analysis by testing cross-reactivity and subtype specificity for a variety of recombinant H1 and H3 HA antigens.

A universal capture array consistent with FIG. 1 was prepared for the testing of cross-reactivity and subtype specificity for a variety of recombinant H1 and H3 HA antigens. The universal capture array included a plurality of positive control spots, a plurality of negative control spots, and nine sub-arrays of capture agent spots. A first sub-array included nine capture agent spots including the same known concentration of anti-A/H1 antibody capable of binding to conformational epitopes of influenza hemagglutinin. A second sub-array included nine capture agent spots including the same concentration of a second anti-A/H1 antibody capable of binding to conformational epitopes of influenza hemagglutinin. A third sub-array included nine capture agent spots including the same concentration of anti-A/H1 antibodies capable of binding to linear epitopes of influenza hemagglutinin. A fourth sub-array included nine capture agent spots including the same known concentration of anti-A/H3 antibody capable of binding to conformational epitopes of influenza hemagglutinin. A fifth sub-array included nine capture agent spots including the same concentration of a second anti-A/H3 antibody capable of binding to conformational epitopes of influenza hemagglutinin. A sixth sub-array included nine capture agent spots including the same concentration of anti-A/H3 antibodies capable of binding to linear epitopes of influenza hemagglutinin. A seventh sub-array included nine capture agent spots including the same concentration of anti-B/Yamagata antibody capable of binding to conformational epitopes of influenza hemagglutinin. An eighth sub-array included nine capture agent spots including the same concentration of anti-B/Yamagata antibody capable of binding to linear epitopes of influenza hemagglutinin. A ninth sub-array included nine capture agent spots including the same concentration of anti-B/Victoria antibody capable of binding to conformational epitopes of influenza hemagglutinin.

The antibody in the first sub-array is anti-CA06/2009 (Cat. # IT-003-001M5) from Immune Technology. The antibody in the second sub-array is C179 (Cat. # M145) from Takara. The antibody in the third sub-array is anit-H1 seasonal (Cat. # IT-003-001M26) from Immune Technology. The antibody in the fourth sub-array is anti-H3 seasonal (Cat. # IT-003-004M1) from Immune Technology. The antibody in the fifth sub-array is anti-H3 F49 (Cat, # M146) from Takara. The antibody in the sixth sub-array is anti-H3 seasonal (Cat. # IT-003-004M2) from Immune Technology. The antibody in the seventh sub-array is anti-B/Wisconsin/ 2010 (Cat. # IT-003-032M7) from Immune Technology. The antibody in the eighth sub-array is anti-B/Wisconsin/2010 (Cat. # IT-003-032M9). The antibody in the ninth sub-array is anti-B/Wisconsin/2012 (Cat. # IT-003-B8M1).

The specificity of the selected antibodies was evaluated using a range of recombinant HA antigens. FIGS. 7A-7V summarize the array response for A/H1 and A/H3 subtypes, and B/Yamagata-like and B/Victoria-like lineages, with each panel of FIGS. 7A-7V corresponding to a different strain as follows:

| FIG. | Strain | Lineage |
|---|---|---|
| 7A | A/New/Caledonia/20/1999 | H1 |
| 7B | A/Solomon Islands/3/2006 | H1 |
| 7C | A/Brisbane/59/2007 | H1 |
| 7D | A/California/04/2009 | H1 |
| 7E | A/California/07/2009 | H1 |
| 7F | A/Duck/Shantou/1283/2001 (H3N8) | H3 |
| 7G | A/Wyoming/3/2003 | H3 |
| 7H | A/New York/55/2004 | H3 |
| 7I | A/Wisconsin/67/2005 | H3 |
| 7J | A/Brisbane/10/2007 | H3 |
| 7K | A/Uruguay/716/2007 | H3 |
| 7L | A/Perth/16/2009 | H3 |
| 7M | A/Victoria/361/2011 | H3 |
| 7N | A/Texas/50/2012 | H3 |
| 7O | A/Texas/50/2012 (wild type) | H3 |
| 7P | B/Malaysia/2506 | B/Victoria |
| 7Q | B/Ohio/1/2005 | B/Victoria |
| 7R | B/Brisbane/60/2008 | B/Victoria |
| 7S | B/Jilin/20/2003 | B/Yamagata |
| 7T | B/Florida/4/2006 | B/Yamagata |
| 7U | B/Wisconsin/1/2010 | B/Yamagata |
| 7V | B/Mass/2/2012 | B/Yamagata |

Over the range of antigens tested (recombinant HA from 1999-2011 origin strains), the microarray exhibited good reactivity, good specificity and no cross-reactivity between the subtypes. It is clear from FIGS. 7A-7V that each strain responds differently to the panel but, in all tested cases, quantification on at least one antibody was possible.

The advantage of including mAbs against both the variable HA1 region of HA as well as the conserved HA2 region of HA is demonstrated in FIGS. 7A-7V for H1 and H3 HAs. For example, only one antibody (the fifth sub-array; the second conformational anti-A/H3 monoclonal antibody described above) reliably responded to all of the H3 strains originating from viruses first isolated over the time period of 2001 to 2012. That antibody is known to bind to the conserved stem region (HA2) of the protein. The same observation is made for recombinant His for viruses isolated over the time period of 1999 through 2009. In this case, the antibody in the second sub-array of the array responded to all H1s and is known to be bind to a conserved region of HA2.

It is worth noting that the multiple capture approach for each subtype or lineage would be impractical for an ELISA system due to reagent cost and low sample throughput per plate (4 samples per plate). In contrast, microarrays are ideally suited to the task due to the sparing use of reagents (pg per spot) and high multiplex capacity. For example, the amount of reagent needed to coat a single ELISA plate can be used to produce over 400 microarrays.

Figure 8A:
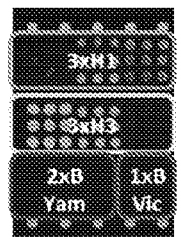
FIGS. 8A-8O show fluorescence signals generated at spots of a universal capture array of FIG. 1 when exposed to trivalent influenza vaccines containing B/Yamagata lineage strains for the time period 20045 to 20089 (FIGS. 8A-8H) and containing B/Victoria lineage strains for the time period 20067 to 201011 (FIGS. 8I-8O).

Multiplex Analysis of Split Vaccines. To test the hypothesis that the present microarray system can serve as a reliable potency assay from year to year, without the need to change the microarray, 16 samples of archived trivalent vaccines were obtained from BEI Resources. The vaccines were produced by top manufacturers over the time span of 2005 through 2011. All vaccines were diluted 1:20 in blocking buffer and analyzed on a multiplexed microarray with sub-arrays arranged as shown in FIG. 8A and consistent with the present disclosure and according to the procedure of Example 1. In addition to the capture agents used in Example 1, the universal capture array also included monoclonal antibodies against B/Yamagata-like lineage and B/Victoria-like lineage HA in order to explore the utility for quantifying all components within quadrivalent vaccines.

Figure 8B:
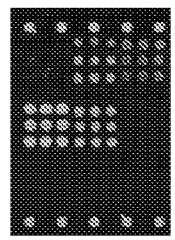
Figure 8C:
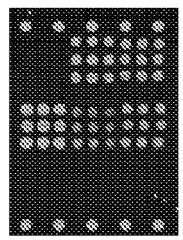
Figure 8D:
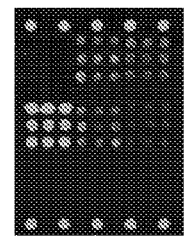
Figure 8E:
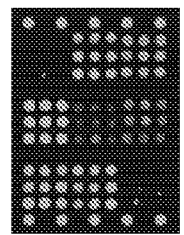
Figure 8F:
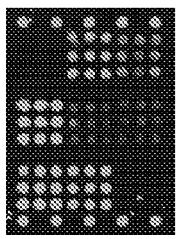
Figure 8G:
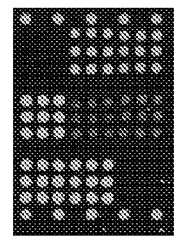
Figure 8H:
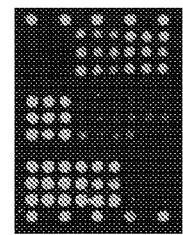
Figure 8I:
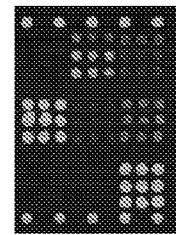
Figure 8J:
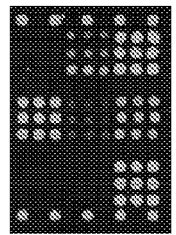
Figure 8K:
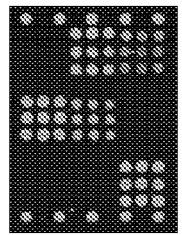
Figure 8L:
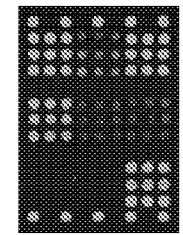
Figure 8M:
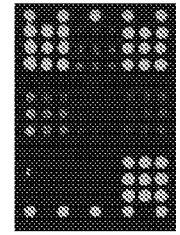
Figure 8N:
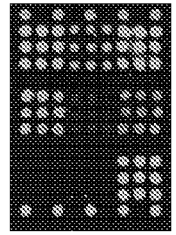
Figure 8O:
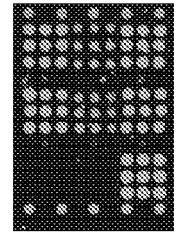

Raw fluorescence images from 14 archived commercial vaccines are displayed in FIGS. 8B-8O, and correspond to the following trivalent vaccines:

The results of this study demonstrate that a universal capture array can be used to provide robust quantification of variable influenza HA. The multiplexed quantification technology provides universality: when one capture agent fails to bind a mutated antigen, other capture agents succeed and are used for quantification.

In addition, while reference antigens are still required for absolute quantification, the production of antigen standards is far less time-consuming than the corresponding antisera required for SRID analysis, and could be accomplished at a

| FIG. | Strain 1 | Strain 2 | Strain 3 | Year | Mfr/Tradename |
|---|---|---|---|---|---|
| 8B* | A/New Cal/20/99 | A/WY/3/2003 | B/Jiangsu/10/2003 | 2004-05 | Sanofi FLUZONE |
| 8C | A/New Cal/20/99 | A/NY/55/2004 | B/Jiangsu/10/2003 | 2005-06 | Sanofi FLUZONE |
| 8D* | A/New Cal/20/99 | A/NY/55/2004 | B/Jiangsu/10/2003 | 2005-06 | Sanofi FLUZONE |
| 8E | A/New Cal/20/99 | A/NY/55/2004 | B/Florida/04/2006 | 2008-09 | Sanofi FLUZONE |
| 8F | A/Brisbane/59/2007 | A/Urug/716/2007 | B/Brisbane/3/2007 | 2008-09 | GSK FLUARIX |
| 8G | A/Brisbane/59/2007 | A/Urug/716/2007 | B/Florida/04/2006 | 2008-09 | CSL AFLURIA |
| 8H* | A/Brisbane/59/2007 | A/Urug/716/2007 | B/Florida/04/2006 | 2008-09 | GSK FLULAVAL |
| 8I | A/New Cal/20/99 | A/Wisc/67/2005 | B/Malaysia/2506/04 | 2006-07 | Sanofi FLUZONE |
| 8J* | A/Solom. Is./3/2006 | A/Wisc/67/2005 | B/Malaysia/2506/04 | 2007-08 | Novartis FLUVIRIN |
| 8K | A/Brisbane/59/2007 | A/Urug/716/2007 | B/Brisbane/60/2008 | 2009-10 | Sanofi FLUZONE |
| 8L | A/CA/7/2009 | A/Vic/210/2009 | B/Brisbane/60/2008 | 2010-11 | Sanofi FLUZONE |
| 8M | A/CA/7/2009 | A/Vic/210/2009 | B/Brisbane/60/2008 | 2010-11 | GSK FLUARIX |
| 8N | A/CA/7/2009 | A/Vic/210/2009 | B/Brisbane/60/2008 | 2010-11 | CSL AFLURIA |
| 8O | A/CA/7/2009 | A/Vic/210/2009 | B/Brisbane/60/2008 | 2010-11 | Sanofi FLUZONE |

*Vaccine contained thimerosal.

FIGS. 8B-8H show results for vaccine formulations ranging from 2004/5 to 2008/9 that contained A/H1, A/H3 and B/Yamagata lineage strains. In all cases but one (FIG. 8B, B/Jiangsu/10/2003), every antigen component within the vaccine was detected and could have been quantified. Since HA from B/Jiangsu/10/2003 was detected within subsequent years' vaccines, it most likely was degraded in the oldest sample. FIGS. 8I-8O show results from vaccine formulations ranging from 2006/7 to 2010/11 that contained A/H1, A/H3 and B/Victoria lineage strains. All antigen components in these trivalent vaccines were detectable on at least one, and often all, of the mAbs on the array.

With carefully selected antibodies, the multiplex system provides redundancy that yields a robust response despite antigenic drift. As noted by Bodle et al. (*Influenza Other Respir. Viruses*, vol. 7(2), pages 191-200 (2013)), in the absence of a dramatic antigenic shift, mAbs exhibit good reactivity for multiple years. Unlike other available technologies, the present microarrays and methods of use thereof allow quantification of HA, even if only one conformational antibody on the array binds well. For example, one of the H1-specific antibodies (the first sub-array) did not perform well for many of the older vaccines tested, but provided excellent fluorescence results with more recent A/H1 strains. Overall, this particular panel of antibodies tested on retrospectively demonstrates remarkably robust response for vaccine formulations produced over a 6-year time span.

number of sites. It is also worth noting that this method could be extended to quantification of other influenza proteins, such as neuraminidase and matrix proteins found in live attenuated and virus like particle vaccines.

Quantitative Analysis of Split Vaccines: Equivalence with SRID.

In order to evaluate the reliability of microarrays of the present disclosure as a potency assay, seven of the archived vaccines spanning the time period of 2009 to 2012 were analyzed for A/CA/2009 H1 HA concentration, CBER reference antigen A/CA/07/2009 (lot number H1-Ag-1107) was used as the calibration standard for all seven vaccines according to guidance documents and procedures available from the FDA. The CBER reference antigen was lysed with Zwittergent 3-14 and each dilution in the calibration set was maintained at 1% Zwittergent. Likewise, 1% Zwittergent was added to the vaccines and maintained at that level for each dilution. Each vaccine was analyzed in duplicate on the array layout consistent with FIG. 1. The mAb printed in the upper left corner of the array (the first anti-A/H1 conformational sub-array described above) is known to be conformational, neutralizing, and specific for HA1 of A/CA H1 pdm, thus, this antibody was the optimal choice for quantification. The results are summarized in Table 1 below:

TABLE 1

Quantification of Hemagglutinin in Archived Influenza Vaccines

| A<br>Sample<br>No. | B<br>BEI Cat. No. | C<br>Mfr. | D<br>Year | E<br>Formula | F<br>Measured [HA]<br>(µg/mL) | G<br>% of<br>original SRID |
|---|---|---|---|---|---|---|
| 1 | NR-20347 | Sanofi | 2009 | Monovalent | 26 | 87 |
| 2 | NR-20083 | Novartis | 2009 | Monovalent | 26 | 87 |
| 3 | NR-31797 | Novartis | 2010/2011 | Trivalent | 33 | 110 |
| 4 | NR-31044 | Sanofi | 2010/2011 | Trivalent | 38 | 127 |
| 5 | NR-31799 | GSK | 2010/2011 | Trivalent | 33 | 110 |
| 6 | NR-31798 | CSL | 2010/2011 | Trivalent | 38 | 127 |
| 7 | NR-36747 | Sanofi | 2011/2012 | Trivalent | 40 | 133 |
| | | | | Average | 33 +/− 6 | 112 +/− 19 |

Each of the vaccines had SRID HA concentrations of 30 µg/mL at release date. Assuming a 20% relative error due to SRIF measurement imprecision, the expected values are 30±6 µg/mL. Four of the values measured by microarray (column F) were within the expected range (Samples Nos. 1-3, 5). Three of the vaccines (Sample Nos. 4, 6, 7) exhibited measured values outside the expected range. A degree of deviation was anticipated due to the age of the vaccines but in general lower values were expected. The slightly higher than expected values may be due to the fact that only most recent CBER reference antigen was used as a standard, rather than using the reference antigen lots specified for each year of the tested vaccine. On average, the microarray yielded a result of 112% of the original SRID value, which is reasonable given the limitations of the study.

Trimer versus Rosette and Other Structures. There has been a long-standing effort to determine what form of HA is actually measured by SRID. The general consensus is that SRID primarily measures the trimeric form of HA but that most vaccines, which are depleted of detergent, contain rosettes (oligomers of the trimer) as the dominant structure for HA. Presumably, the oligomeric form is in equilibrium with the trimeric form and that equilibrium is shifted toward the trimeric form when Zwittergent 3-14 is used at 1%, which is the case for the SRID measurement.

Gupta (CBER/FDA Presentation at PhRMA Annual Flu Meeting, available at by request from CBER/FDA, reported that the trimeric form of HA yielded a factor of ~3 times higher signal in SRID than the oligomer. When the vaccines summarized in FIGS. 8A-8O are analyzed without Zwittergent present, the signal intensity on the A/CA-H1 specific mAb is ~5× higher. Consistent with the currently accepted understanding, the hypothesis is that the trimeric form of HA is measured in the presence of Zwittergent but the oligomeric form is measured in the absence of Zwittergent. The signal is likely higher for the oligomeric form due to a higher degree of labeling on each captured oligomer. Assuming 5-6 trimers per rosette and no significant loss in binding density at the surface, one would expect higher labeling density (i.e., 5-6× higher signal), which is consistent with the present observations.

Accuracy and Precision. To examine the accuracy and precision of replicate microarray experiments on a trivalent vaccine formulation, each component within a trivalent formulation was analyzed in triplicate (3 different trials). The measured values from all antibodies for each subtype (e.g., the first, second, and third sub-arrays) were averaged to obtain the HA concentration.

Figure 9:
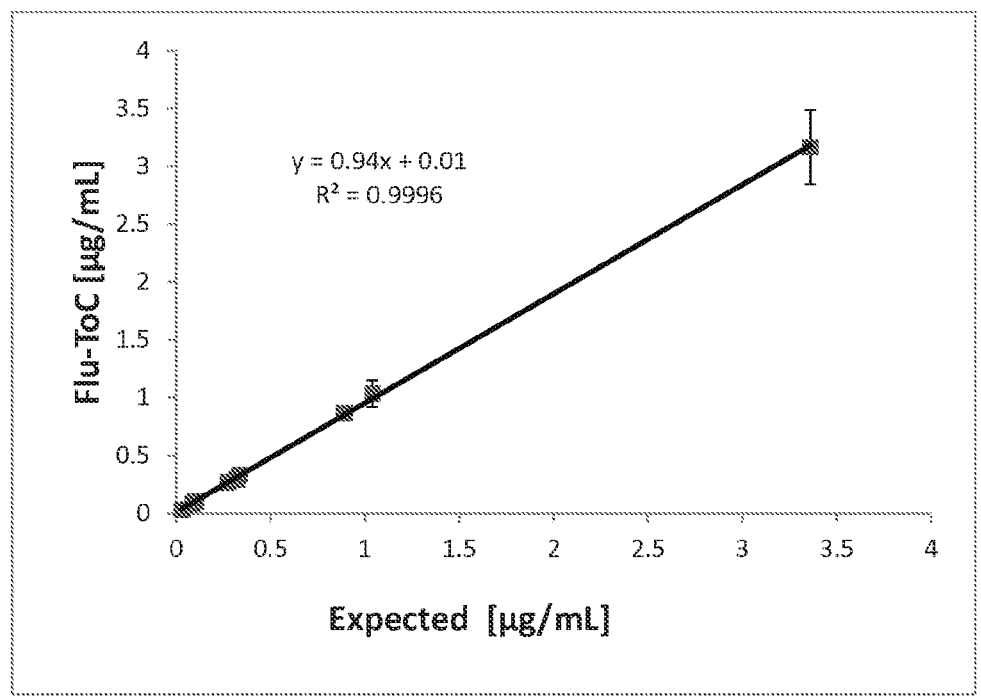
FIG. 9 shows an average measured hemagglutinin concentration as a function of the expected hemagglutinin concentration for three replicate experiments for each of three different recombinant hemagglutinin proteins, specifically. A/CA, A/Victoria, and B/Wisc.

FIG. 9 is a plot of the overall average measured value for three different antigens from the three trials as a function of the expected value, which are also found in Table 2 below. The solid line in the graph is a linear regression that demonstrates good correlation ($R^2>0.99$) and linearity (slope=0.94) between the measured and expected values.

Table 2 summarizes the quantitative results along with an assessment of accuracy (e.g., the difference between the measured value and the expected value) and precision. Overall the accuracy for simultaneous quantification of all three HA proteins was excellent, with an average error of ~4% relative to the expected value. The reproducibility between trials was also quite good, with an average relative standard deviation of ~9%. This study demonstrates that microarrays consistent with the present disclosure can be used to accurately quantify multivalent recombinant vaccines.

TABLE 2

| Sample ID | Antigen | Known Conc. (µg/mL) | Trial 1 | Trial 2 | Trial 3 | Avg. Conc. (µg/mL) | Accuracy (% error) | Reproducibility (Inter-trial % RSD) |
|---|---|---|---|---|---|---|---|---|
| Trivalent 1 | H1/CA | 0.32 | 0.32 ± 0.02 | 0.33 ± 0.02 | 0.23 ± 0.02 | 0.30 | 7.1 | 18 |
| | H3/VIC | 1.04 | 1.1 ± 0.1 | 1.1 ± 0.1 | 0.9 ± 0.1 | 1.0 | 2.3 | 8.2 |
| | B/WISC | 3.36 | 3.4 ± 0.9 | 3.3 ± 0.7 | 2.8 ± 0.4 | 3.1 | 7.3 | 10 |
| Trivalent 2 | H1/CA | 0.085 | 0.083 ± 0.003 | 0.079 ± 0.003 | 0.071 ± 0.007 | 0.077 | 8.8 | 7.9 |
| | H3/VIC | 0.275 | 0.26 ± 0.04 | 0.27 ± 0.03 | 0.27 ± 0.05 | 0.27 | 2.9 | 2.1 |
| | B/WISC | 0.89 | 0.8 ± 0.1 | 0.9 ± 0.2 | 0.9 ± 0.1 | 0.8 | 5.5 | 2.5 |
| Trivalent 3 | H1/CA | 0.032 | 0.035 ± 0.002 | 0.031 ± 0.003 | 0.026 ± 0.002 | 0.031 | 3.3 | 16 |
| | H3/VIC | 0.103 | 0.11 ± 0.001 | 0.10 ± 0.02 | 0.09 ± 0.01 | 0.10 | 0.8 | 11 |
| | B/WISC | 0.334 | 0.36 ± 0.03 | 0.33 ± 0.03 | 0.30 ± 0.05 | 0.33 | 0.1 | 8.8 |

Example 3

Essential for any potency assay is that it be stability indicating. As vaccines degrade over time, the SRID measured HA concentration decreases. Since SRID is believed to be directly correlated with immunogenicity, the decrease in measured concentration corresponds to lower potency.

Figure 11:
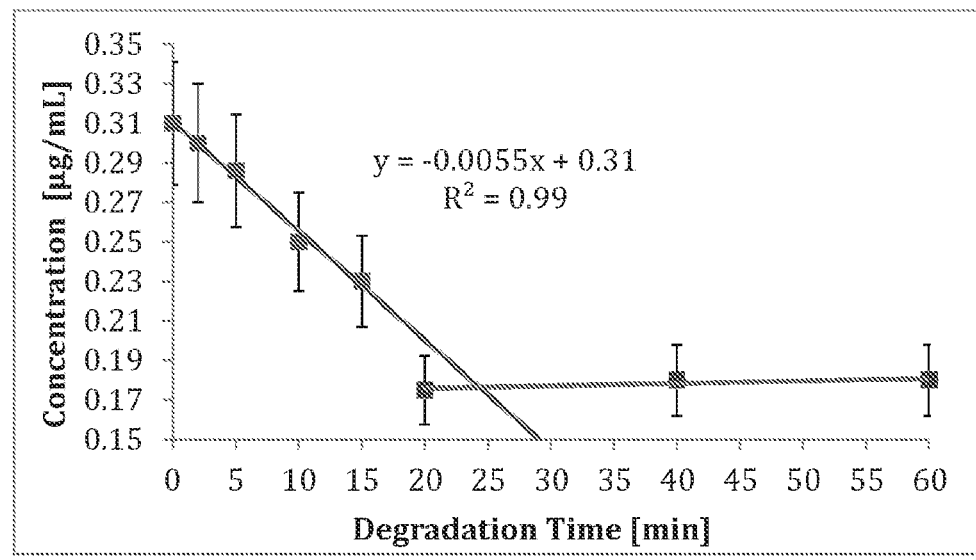
FIG. 11 shows degradation of reference antigen A/CA/07/2009 when exposed to 50° C. for up to 60 minutes, as measured by an array consistent with FIG. 1 including conformational and neutralizing capture agents.

The microarrays of the present can also characterize stability indicating behavior. As one test that function, a CBER reference antigen (A/CA/07/2009) was lysed with 1% Zwittergent 3-14, aliquoted, and each aliquot exposed to 50° C. for a different amount of time (0 min to 60 min). On the array, A/CA H1 specific capture mAb (conformational and neutralizing) was used for quantification. The measured concentration as a function of exposure time is shown in FIG. 11. As expected, the measured concentration decreased with exposure time to elevated temperature. The concentration decreased ~45% within the first 25 minutes followed by a steady state measured concentration. This trend is qualitatively similar to the SRID and ELISA results published by Hashem et al. for A/CA/07/2009, who observed a ~20% decrease in SRID measured concentration and a ~90% decrease for ELISA measured concentration for exposure to 50° C. for 1 hour.

Figure 12:
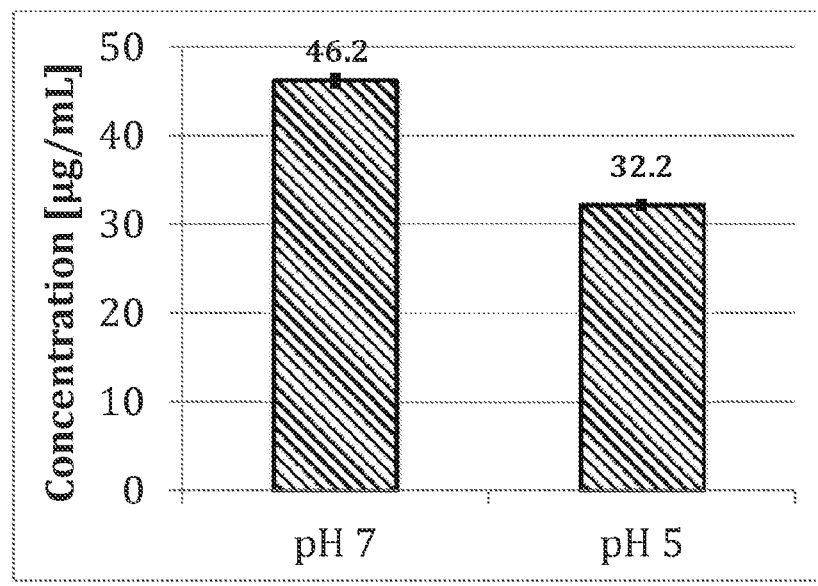
FIG. 12 shows the concentration of reference antigen A/CA/07/2009 when lysed at pH 7.2 after being exposed for 30 minutes to acidic (pH 5.0) medium compared to control ("pH 7"), as measured by an array consistent with FIG. 1.

Stability is also commonly tested at low pH where hemagglutinin is known to undergo significant conformational changes. With respect to SRID measurements, the result is a decrease in measured concentration of the trimeric form. To evaluate the response of microarrays of the present disclosure, lysed A/CA/07/2009 was exposed to pH 5.0 for 30 minutes, neutralized back to pH 7.2, Zwittergent added to maintain 1%, and analyzed on the array. Results were compared to an equivalent concentration aliquot that had not been exposed to low pH. The results are compared in FIG. 12. A decrease of ~30% in measured concentration was observed, which is qualitatively similar to the SRID and ELISA results published by Hashem et al. In their work, the SRID value decreased ~80% and the ELISA value decreased ~100% upon a 1 hour exposure to pH 5.

As a demonstration of potential insight provided by using a combination of conformational and linear capture antibodies, when the pH study was conducted without 1% Zwittergent present, the signal intensity increased as the pH was lowered. For A/Brisbane/10/2007 (H3) the response on both conformational and linear mAbs (both known to bind to HA1) increased by 17× in the case of the linear mAb and 3× for the conformational mAb. One possible explanation for this behavior is based on structure proposed by Fontana et al. for the post-fusion form and intermediates. At low pH the head groups of the trimer open and become less sterically hindered, which may enable a higher binding density, especially for the linear mAb. In addition, HA forms rosettes in the absence of Zwittergent which, as we argued previously, can lead to 5-6× higher signal on the array relative to trimers. Presumably, these changes in structure offset to some degree the loss of conformation due to pH, which is consistent with the linear mAb binding increasing significantly more than for the conformational mAb.

Figures 10A, 10B:
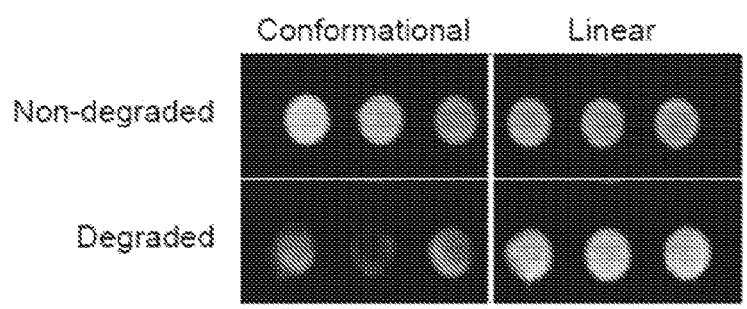
FIGS. 10A-10B show fluorescence signals generated at spots of universal capture arrays used to quantify degradation of viral protein in a vaccine material, and quantification of signals according to one embodiment of the present disclosure.

FIG. 10A summarizes another example of the unique stability-indicating capability of the universal array that is based on the use of both conformational and linear mAbs (sub-arrays H and I in FIG. 1). In this case, rHA from B/Massachusetts/02/2012 oxidized in a 1% $H_2O_2$ solution (3 hours at 4° C.) demonstrates a decrease in signal on the conformational monoclonal antibody and an increase in signal on the linear mAb relative to the non-oxidized protein response. Fluorescent images for non-oxidized and oxidized samples are shown in the bottom panel of FIG. 10B. Quantification of the fluorescence signals show a statistically significant decrease in binding to the conformational epitope (−53%) and a statistically significant increase in binding to the linear epitope (+30%) after oxidation of the sample. Thus a universal capture array that comprises sub-arrays targeting linear and conformational epitopes of influenza HA protein can be used in a unique way to quantify degradation of a vaccine material.

Example 4

Virus-Like Particles (VLPs)

Influenza vaccine produced in new production platforms, such as virus-like particles produced in plants, will require a new potency assay since the glycosylation pattern for these proteins can, for some strains, prevent the application of SRID. To demonstrate the potential of the universal array, flu VLPs were analyzed on the universal array. Each sample was split with 1% tergitol at room temperature for 30 minutes. CBER reference antigens were used as standards for calibration. The results are summarized in Table 3, and demonstrate that the microarrays of the present technology generate a result equivalent to SRID for these new vaccines.

TABLE 3

Microarray Accuracy vs. SRID

| Formulation | Protein by BCA (µg/mL) | Potency by SRID (µg/mL) | [HA] by Microarray (µg/mL) | Precision (RSD) | Accuracy (% of SRID) | CBER Standard |
| --- | --- | --- | --- | --- | --- | --- |
| A/H3 VLP BDS (n = 3) | 296 | 190 | 170 +/− 13 | 7.6% | 89 | A/Texas/50/2012 X-223A Lot 75 |
| B/Brisbane VLP BDS (n = 17) | 410 | 217 | 216 +/− 7 | 3.2% | 100 | B/Bris/60/2008 Lot 68 |
| A/H1 VLP BDS (n = 18) | 259 | 212 | 231 +/− 15 | 6.5% | 109 | A/Ca/07/2009 X-181 Lot H1-Ag-1107 |

Example 5

A universal capture array for quantifying the concentration and/or degradation of influenza proteins during vaccine manufacturing processes was prepared including a microarray consistent with FIG. 1. Sets of two chips, each containing 16 microarrays, as schematically shown in FIG. 4, were used for this study. The universal capture array included a plurality of positive control spots, a plurality of negative control spots, and nine sub-arrays of capture agent spots. A first sub-array included nine capture agent spots including the same known concentration of anti-A/H1 antibody capable of binding to conformational epitopes of influenza hemagglutinin. A second sub-array included nine capture agent spots including the same concentration of a second anti-A/H1 antibody capable of binding to conformational epitopes of influenza hemagglutinin. A third sub-array included nine capture agent spots including the same concentration of anti-A/H1 antibodies capable of binding to linear epitopes of influenza hemagglutinin. A fourth sub-array included nine capture agent spots including the same known concentration of anti-A/H3 antibody capable of binding to conformational epitopes of influenza hemagglutinin. A fifth sub-array included nine capture agent spots including the same concentration of a second anti-A/H3 antibody capable of binding to conformational epitopes of influenza hemagglutinin. A sixth sub-array included nine capture agent spots including the same concentration of anti-A/H3 antibodies capable of binding to linear epitopes of influenza hemagglutinin. A seventh sub-array included nine capture agent spots including the same concentration of anti-B/Yamagata antibody capable of binding to conformational epitopes of influenza hemagglutinin. An eighth sub-array included nine capture agent spots including the same concentration of anti-B/Yamagata antibody capable of binding to linear epitopes of influenza hemagglutinin. A ninth sub-array included nine capture agent spots including the same concentration of anti-B/Victoria antibody capable of binding to conformational epitopes of influenza hemagglutinin Eight microarrays were used for calibration using recombinant hemagglutinin reference standards; samples obtained from various stages of a typical vaccine manufacturing process were processed on 8-24 microarrays.

For recombinant proteins, the assay uses a combination of label antibodies, each of which are conjugated with a fluor that emits in the "Cy3" channel. Typically, a single polyclonal label (ToC 5514, InDevR) can be used to quantify all components of a quadrivalent HA mixture from split viruses and virus-like particles. However, recombinant HA requires two additional subtype-specific labels. The H1-specific label (ToC 5512, InDevR) is conformational, neutralizing, and is known to bind to the F sub-domain on HA2. The H3-specific label (5513, lnDevR) binds to a conserved region of HA2 but is non-neutralizing. Recombinant B HA proteins are labeled with the polyclonal antibody.

For this example, only the conformational, neutralizing capture antibodies were used for quantification. Specifically, antibodies in the first, fourth, fifth, and ninth sub-arrays were used to quantify H1, H3, B/Yam-like, and B/Vic-like strains. While not included in this study, the additional capture antibodies for each strain can be used to provide complimentary information and insight into response to environmental conditions.

The microarray-containing slides were allowed to come to room temperature prior to pre-processing in Wash Buffer 1 (ToC-5532, lnDevR) for 5 minutes on an orbital shaker (50 rpm). The slides were ready for use after drying. Since the quantification range is typically below 3 µg/mL, samples were diluted into Blocking Buffer (ToC-5531, InDevR) to yield final concentrations within the quantification range. Sample and standard volumes of 50 µL each were placed directly onto respective arrays and the slide incubated in a humidity chamber at room temperature for one hour. After incubation, sample solutions were removed by pipette and the slides washed in Wash Buffer 1 for 1 minute and Wash Buffer 2 (ToC-5533, InDevR) for 5 minutes. After removal of excess wash solution, the appropriate fluor-conjugated label antibody and positive control label (ToC-5512-15, InDevR) were added and the slide incubated at room temperature for 30 minutes. Excess label solution was removed and the slide was washed sequentially with Wash Buffers 1 and 2. Excess liquid was removed prior to imaging on a fluorescence microarray scanner (Vidia, InDevR). Imaging was conducted using excitation centered at 530 nm and emission on the "Cy3" channel at a typical collection time of 1 s per array. With this protocol, 8 standards and 24 samples can be processed within 3 hours.

Calibration was accomplished with glycerol reference standards of recombinant HA (Protein Sciences Corporation) from A/CA/07/2009, A/TX/50/2012 (H3), B/Brisbane/60/2008, B/Mass/02/2012, each of which were previously calibrated by SRID against CBER standards. For the blinded study, each sample batch was calibrated against the recombinant reference antigens serially diluted into Blocking Buffer to yield an 8 point standard range, including a blank. A typical calibration concentration range was zero to 1-3 µg/mL, with the lowest concentration being ~0.02 µg/mL.

Automated Quantification Algorithm. Quantitative data were extracted using a software package and results were obtained using an automated algorithm. The image analysis program automatically: i) extracts the median digital signal from each spot in the image, ii) determines the median value from each set of 9 replicate spots per capture antibody, iii) determines the median background value from 20 spots, iv) normalizes the analyte signal (median value) to the internal positive control, v) automatically plots and analyzes calibration data from the 8 calibration arrays (fluorescence signal as a function of HA concentration), vi) determines linear response ranges within the calibration curve via linear regression analysis, and vii) uses the linear regression fit to back-calculate concentrations for samples.

Normalization of the signal on each array using a positive control was used to account for array-to-array variability during manufacture and/or processing. The median value of ten positive control spots (10) was used for normalization. Specifically, the median background value was subtracted from the median sample value, the result multiplied by 100 and divided by the background-corrected median positive control value. The background value on each array was determined from the median of 20 non-spotted areas at various but specific locations on each array. We note that median values are used for all calculations, rather than the mean, as a more effective way to eliminate statistical outliers. Since array processing can sometimes lead to non-relevant "bright spots", outliers from multiple measurements (9 replicates in the case of samples, 10 replicates for positive (internal) controls, and 20 replicates for the background) can more readily be discarded.

The "4 point" linear region approach was used in in order to accommodate typical binding curves without relying on a multi-parameter non-linear regression. Thus, for each calibration curve there may be multiple linear regions. The quantification algorithm automatically assesses four separate criteria to determine the suitability of a particular linear range for a specific sample: specifically, 1) a linear region is defined as 4 adjacent points that yield a Pearson's correlation coefficient (R)>0.97, 2) a slope>10, 3) the normalized sample signal must fall within the 4 point range, and 4) the normalized sample signal must be above the quantification limit. The quantification limit is defined by the normalized signal for the blank plus a multiple of the standard deviation in the blank, typically 10×. If a sample signal meets the criteria for multiple linear regions on a curve, the average value is reported along with the measured precision.

Fluorescence signals are shown in FIGS. 13A-13O as follows: fluorescence signals of subtypes and lineages of influenza: A/CA H1 are shown in FIGS. 13A-13D; fluorescence signals from subtype A/TX H3 are shown in FIGS.

13E-13H; fluorescence signals from subtype B/Mass/Yamagata-like are shown in FIGS. 13I-13L; and fluorescence signals from subtype and B/Brisbane/Victoria-like are shown in FIGS. 13M-13O), each at four different stages of a typical vaccine manufacturing process: at the crude extract stage (FIGS. 13A, 13E, 13I and 13M), after process intermediate 1 (FIGS. 13B, 13F, 13J and 13N), after process intermediate 2 (FIGS. 13C, 13G and 13K; note that no sample corresponding to B/Brisbane/Victoria-like was obtained at the process intermediate 2 stage), and in the bulk drug substance form (FIGS. 13D, 13H, 13L and 13O). In this particular set of sub-arrays, the linear antibody for the H1 monoclonal antibody (top right sub-array) exhibited cross-reactivity with the polyclonal antibody label due to some degradation of the capture agent monoclonal antibodies.

the second sub-array did not capture antigen from the crude extract, although it did capture antigen at the other three manufacturing stages.

Figure 15:
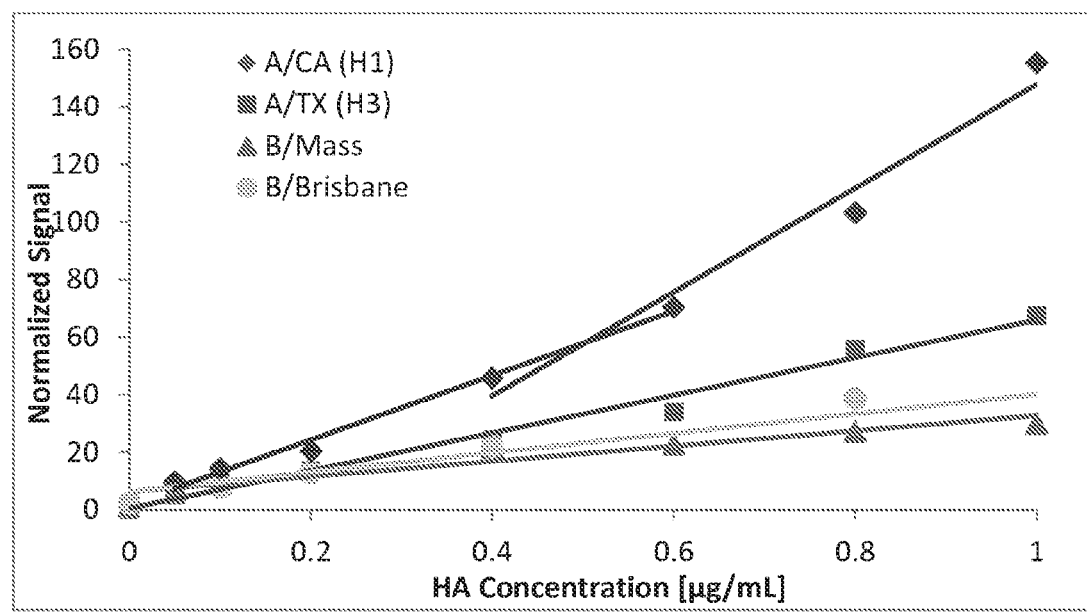
FIG. 15 shows representative calibration curves for recombinant hemagglutinin obtained from four reference strains. Two linear four-point regions for A/CA (H1) strain are illustrated (diamonds).

Representative calibration curves generated using recombinant antigens of known concentration and utilized to determine the unknown concentrations of the antigens shown in the fluorescence images in FIGS. 13A-13O are shown in FIG. 15. The quantification limits and ranges were determined to be ~0.025-1 µg/mL for H1 and H3 rHA and ~0.1-3 µg/mL for B rHA. The sensitivity and range for H1 and H3 are particularly good, with a span of 40×. For comparison, the typical quantification range for SRID is ~3-30 µg/ml (10× span) and 2.5-10 for ELISA with CBER reference antisera as the capture agent.

Table 4 summarizes the results prior to un-blinding of the sample concentrations.

TABLE 4

Quantification of HA during Vaccine Manufacturing Process.

| Protein | Type | Sub-array # | ToC (µg/mL) | Precision (% RSD) | N | SRID (µg/mL) | ELISA (µg/mL) | BCA (µg/mL) |
|---|---|---|---|---|---|---|---|---|
| B/Brisbane | Crude | 9 | 39 ± 6 | 16 | 11 | 31 | 34 | 768 |
| | PIM 1 | 9 | 227 ± 47 | 20 | 12 | 133 | 224 | 167 |
| | BDS | 9 | 713 ± 77 | 11 | 12 | 434 | 823 | 707 |
| B/Mass | Crude | 7 | 0.42 ± 0.2 | 48 | 7 | 18 | <2.5 | 748 |
| | PIM 1 | 7 | 17 ± 7 | 39 | 4 | 80 | 8 | 326 |
| | PIM 2 | 7 | 512 ± 139 | 27 | 7 | 537 | 191 | 817 |
| | BDS | 7 | 367 ± 81 | 22 | 5 | 282 | 566 | 599 |
| A/CA H1 | Crude | 1 | 28 ± 16 | 56 | 10 | * | 49 | 2078 |
| | PIM 1 | 1 | 261 ± 39 | 15 | 5 | 216 | 122 | 291 |
| | PIM 2 | 1 | 3300 ± 440 | 13 | 6 | 640 | 2479 | 1836 |
| | BDS | 1 | 793 ± 91 | 12 | 5 | 337 | 599 | 530 |
| A/TX H3 Wild-type | Crude | 4 | 11 ± 5 | 40 | 8 | 94 | 22 | 917 |
| | PIM 1 | 4 | 170 ± 15 | 9.0 | 6 | 344 | 138 | 420 |
| | PIM 2 | 4 | 776 ± 83 | 11 | 6 | 1139 | 716 | 887 |
| | BDS | 4 | 172 ± 10 | 5.9 | 6 | 501 | 534 | 566 |
| A/TX H3 | Crude | 4 | 35 ± 8 | 22 | 7 | 118 | 19 | 1000 |
| | PIM 1 | 4 | 254 ± 50 | 19 | 8 | 775 | 113 | 572 |
| | PIM 2 | 4 | 1115 ± 168 | 15 | 6 | 2531 | 291 | 1180 |
| | BDS | 4 | 506 ± 36 | 7.1 | 2 | 674 | 339 | 525 |

Qualitatively, FIGS. 13A-13O demonstrate that the microarrays of the present disclosure can be used at all stages of the manufacturing process, including for analyzing crude extracts from cell culture where the antigen concentration is low and "contaminant" levels are high. Comparable analyses of crude cell culture extracts using ELISA suffer from relatively high limits of quantification due to non-specific binding on the reference anti-sera used for coating.

Specificity for each subtype is high, as shown in FIGS. 13A-13O. More specifically, distinct response to B/Yamagata-like and B/Victoria-like is clearly present, as evidenced by the lack of signal on capture agent antibodies for other subtypes. This level of specificity enables analysis of samples in either monovalent formulations or multivalent formulations (multiplexed). Fluorescence signals for the crude cellular extract samples (FIGS. 13A, 13E, 13I and 13M) exhibited good signal and minimal background. Signals were strong and backgrounds were weak for other process steps too, including through the bulk drug substance manufacturing stage.

Figure 14:
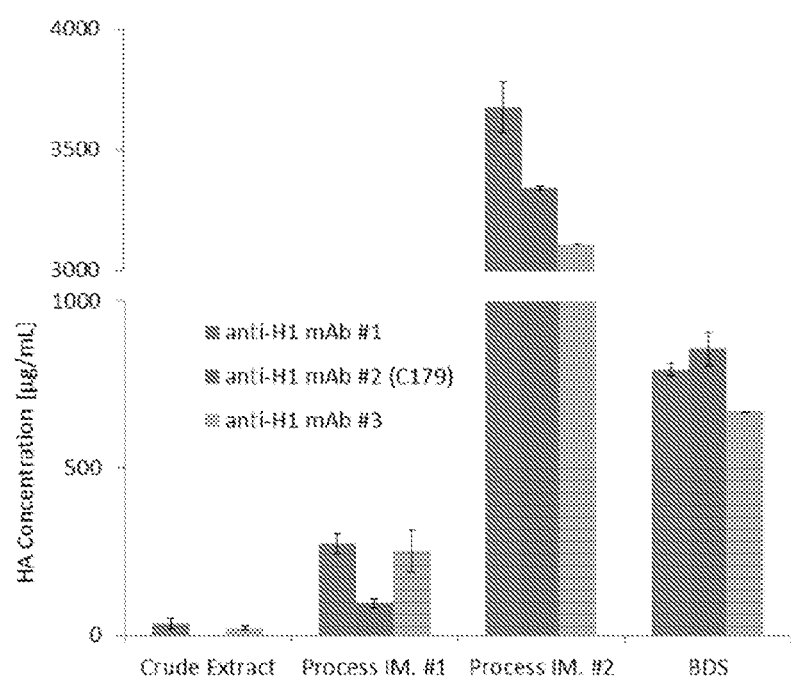
FIG. 14 shows quantitative results from the arrays shown in FIGS. 13A-13D in terms of the measured hemagglutinin concentrations.

FIG. 14A shows the raw fluorescence intensities measured for each of three capture agents at each of the four stages of vaccine manufacture. FIG. 14B shows the calculated hemagglutinin concentration corresponding to the raw intensities of FIG. 14A for each monoclonal antibody at each stage of vaccine manufacture. Notably, the anti-H1 mAb in The HA content for each strain measured at each stage in the manufacturing process is shown in column 4 ("ToC") along with measured error. The values are weighted averages from replicate studies. The average relative error (precision) over all measurements was 21%; however, not surprisingly, the average relative error was highest for the crude extracts (36%). Excluding crude extracts, the average relative error was 16%. For BDS samples the average relative error was 12%. Table 4 also reports quantification results using ELISA, SRID and BCA methodologies for comparison.

Example 6

Figure 16A:
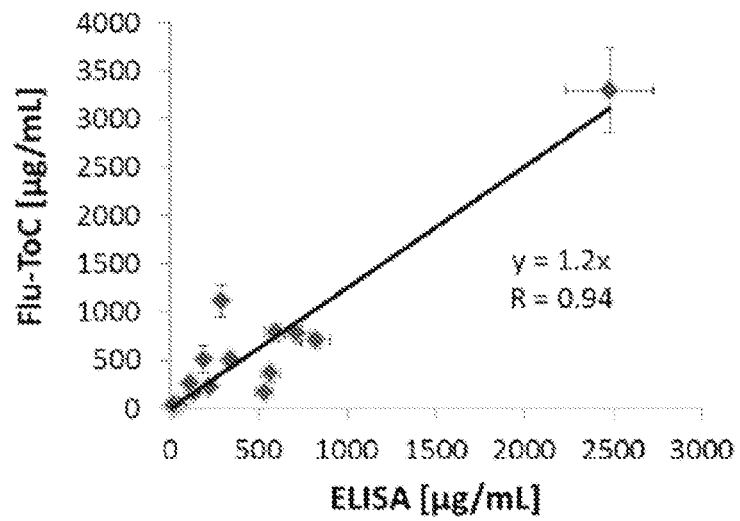
FIGS. 16A-16B plot measured hemagglutinin protein concentrations using a microarray consistent with the present disclosure (y-axis) compared to the concentration of hemagglutinin determined by ELISA.
Figure 16B:
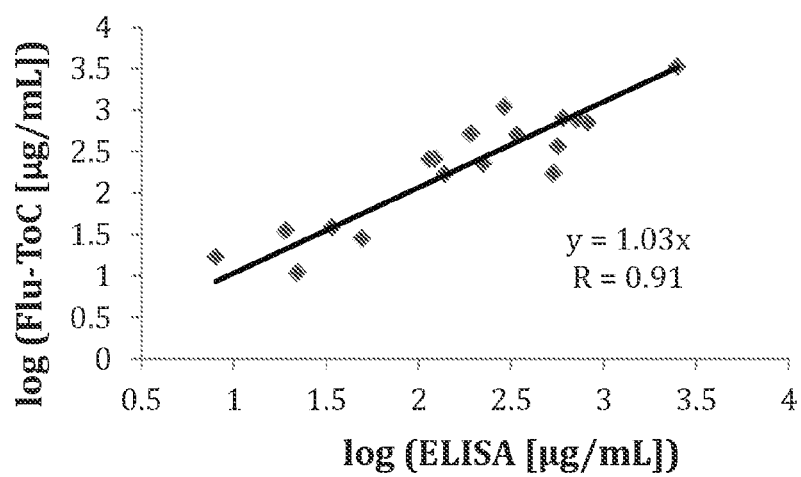

FIGS. 16A-16B show plots of HA content as determined using the microarray and experiment described above in Example 5 (abbreviated "Flu-ToC") versus ELISA in linear space (FIG. 16A) and log space (FIG. 16B). The measurement error for the microarray is included and ±10% relative error is assumed for ELISA. Eighteen of the 19 samples tested are included in the plots, One sample was not included as the concentration measured by the microarray was below the quantification limit for ELISA. The solid lines represent linear regressions to the data. For the linear graph (FIG. 16A), the regression was fitted through 0,0 in order to enable more accurate assessment of residuals. The slope with that fit is 1.2 with a Pearson's correlation coefficient of 0.94. Based on residuals analysis, none of the points could be discarded as outliers.

While the relatively high correlation coefficient between the microarray and ELISA indicates a good correlation, another test of a linear relationship is to plot the log of each set of values against each other. In log space, a linear relationship (neglecting the intercept) should yield a slope of 1. As shown in FIG. 16B, that is indeed the case for log(Flu-ToC) values versus log (ELISA). Thus, one may conclude that there is a linear relationship between HA content determined by the present microarray and ELISA (with CBER reference antisera as the capture agent). Based on the slope of the linear graph, in general the microarray yields slightly (~20%) higher values.

Example 7

Figure 17A:
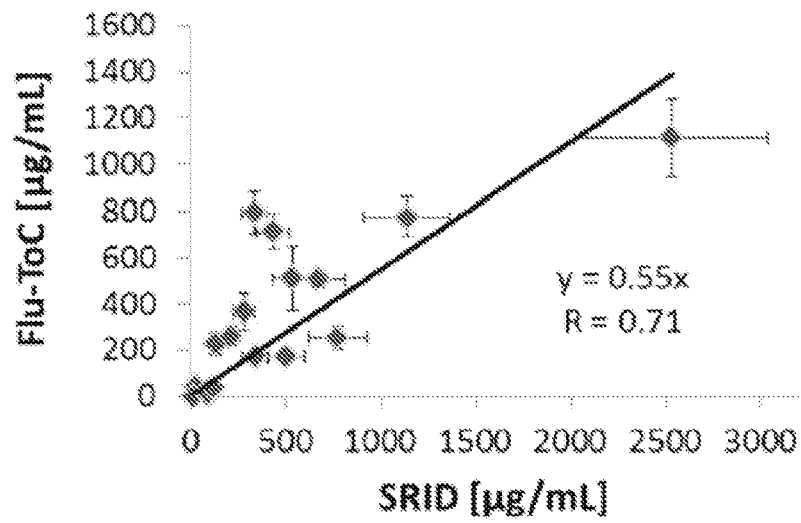
FIGS. 17A-17B plot measured hemagglutinin protein concentrations using a microarray consistent with the present disclosure (y-axis) compared to the concentration of hemagglutinin determined by SRID.
Figure 17B:
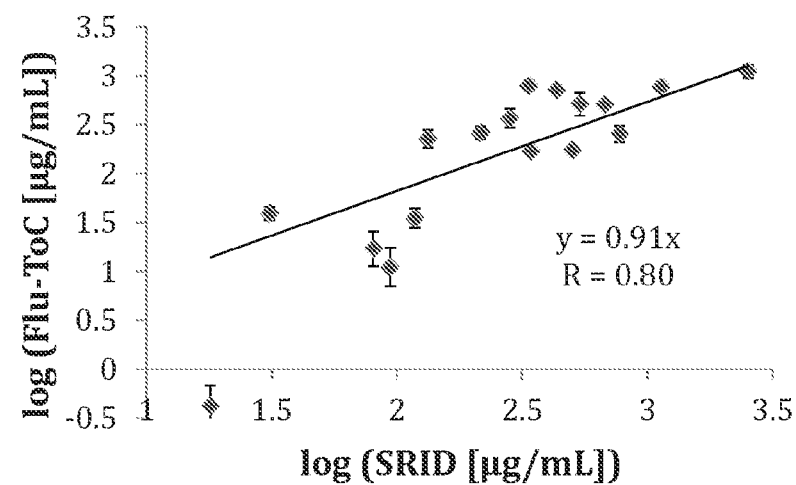

The relationship between the microarrayexperiment described in Example 5 (abbreviated "Flu-ToC") and SRID is shown in FIGS. 17A-17B. Measured error in included for the microarray and 20% relative error was assumed for SRID. Only one data point was excluded as an identified statistical outlier. In fact, since both the microarray and ELISA yielded much higher values for the NCA process intermediate 2, it is speculated that the SRID value is incorrect. The linear regression (FIG. 17A) exhibits a slope of 0.55 and a Pearson's correlation coefficient of 0.71. The statistical significance of the correlation is reasonable, with $t(15)=3.9$, $p<0.002$. Furthermore, the log-log plot (FIG. 17B) exhibits a slope of 0.91 with $R=0.80$, which is also reasonable. Therefore, it is concluded that the results from this blinded study demonstrate a direct linear relationship exists between HA content measured by the present microarray and SRID.

While the slope of the linear plot (FIG. 17A) indicates a lower HA content measured by the microarray, it is important to note that the microarray measurements were conducted in the absence of Zwittergent 3-14 (which is present in the SRID measurement). Preliminary studies indicate that analysis using the microarray can be conducted with 1% Zwittergent 3-14 present; however, additional studies to quantify the effects are ongoing.

Example 8

The Bicinchoninic Acid (BCA) assay is widely used in the flu vaccine industry as a non-specific measure of total protein content. When combined with SDS-PAGE densitometry, which is used to determine purity of the protein of interest, BCA can serve as a means to create a primary standard reference antigen. In fact, CBER employs a similar approach to characterize seasonal reference antigens. It is therefore important that alternatives to SRID exhibit good correlation with HA content measured by purity-adjusted BOA (paBCA). The right-most column in Table 6 summarizes the unadjusted BOA values obtained as part of the experiment described in Example 5 (paBCA data not shown). The results from linear regression analysis of Flu-ToC, ELISA and SRID plotted against the paBCA values are tabulated in Table 6. For Flu-ToC, the statistical outlier identified with respect to SRID (i.e., SRID 640 µg/mL, Flu-ToC 3,300 µg/mL in Table 4) was not included in the regression. When the intercept is forced through zero, both Flu-Toe; and ELISA exhibited a slope close to 1 and reasonable R values, indicating good correlation. Somewhat surprisingly, both immunoassays exhibited better correlation with paBCA than did SRID. With the y-intercept included as a variable in the regression, Flu-ToC; yields a slope of 1, a small intercept, and an R value of 0.90, all of which are slightly better than the trends exhibited by ELISA and SRID.

TABLE 6

Tabulated Results from paBCA Correlation Analysis

| | Zero Intercept | | With Intercept | | |
|---|---|---|---|---|---|
| | Slope | R | Slope | Intercept | R |
| ToC | 0.94 | 0.89 | 1.0 | 41 | 0.90 |
| ELISA | 1.0 | 0.83 | 1.2 | 154 | 0.85 |
| SRID | 1.0 | 0.60 | 0.91 | 85 | 0.61 |

Example 9

Figure 18A:
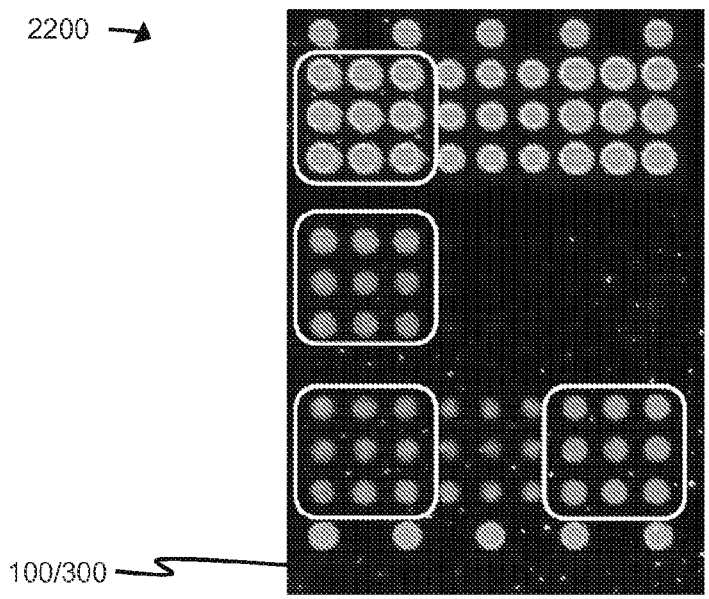
FIGS. 18A-18B show representative fluorescence images corresponding to a multiplexed bulk drug substance (FIG. 18A) compared to the individual hemagglutinin components of the multiplexed substance (FIG. 18B) using a microarray consistent with the present disclosure.

As previously mentioned, a significant advantage of the present microarray technology over ELISA is the ability to conduct simultaneous analysis of all components in the finished drug product. A multiplexed sample was prepared by mixing known amounts of each of four strains (A/CA (H1), A/TX (H3); B/Mass, and B/Bris). FIG. 18A illustrates a representative image of multiplexed analysis of all components within a quadrivalent formulation (constructed from a mixture of monovalent BDS) using a microarray 400 consistent with the present disclosure. The white boxes of microarray 400 highlight four sub-arrays, each of which was used to quantify one type of hemagglutinin in the multiplexed sample. Sample processing, data collection and processing were all performed consistent with the procedures outlined in Example 1.

Figure 18B:
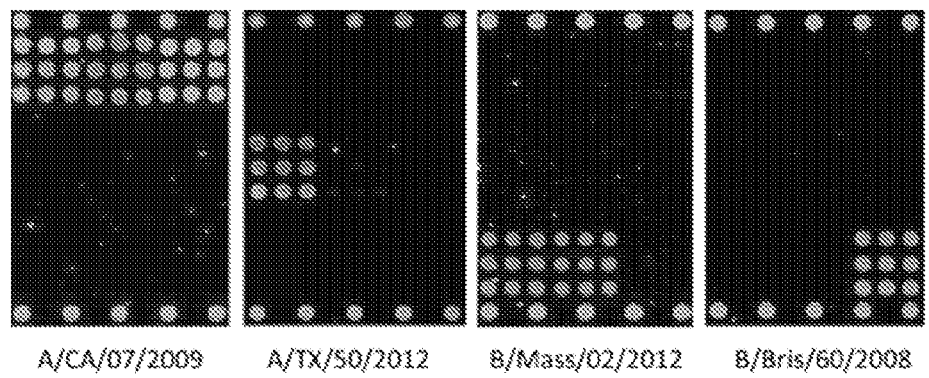

FIG. 18B shows fluorescent signals generated on a microarray 400 from each of the separate hemagglutinin sources (e.g., strains) for comparison. Quantification results are shown in Table 5, and compare data obtained from the multiplexed sample (e.g., "Quadrivalent") to data obtained from the four individual strains (e.g., "Monovalent").

TABLE 5

Quantification of rHA in a Multiplexed Sample

| rHA | Monovalent | Quadrivalent |
|---|---|---|
| A/CA (H1) | 793 ± 91 | N/A |
| A/TX (H3) | 172 ± 10 | 203 ± 24 |
| B/Mass | 367 ± 81 | 267 ± 32 |
| B/Bris | 713 ± 77 | 665 ± 80 |

Multiplexed quantification was conducted 3 months after the initial measurements but, with the exception of A/CA HA for which a new label antibody was tested, within error the results were equivalent to those reported for the monovalent BDS. This level of multiplexing is not possible with ELISA. The fact that the array-based platform can be used at all stages of vaccine production, from the crudest samples through the finished drug product, is perceived to be of benefit in regulated environments.

Example 10

To arrive at a universal capture array in accordance with another embodiment of the current invention, a wide range of antibodies, including purified monoclonals, polyclonals, and antisera are evaluated for subtype specificity for use as capture agents. Antibodies are selected from a wide range of commercial sources for the ability to bind hemagglutinin from potentially pandemic strains of influenza, including but not limited to influenza A/H1, A/H2, A/H3, A/H5, A/H7, and A/H9.

Antibodies are diluted into spotting buffer at a range of concentrations, and each concentration spotted onto epoxy-coated glass slides (Nexterion Slide E, Schott; Applied Microarrays Inc.). Performance is evaluated by quantifying the response to potentially-pandemic subtype-specific HA antigens. Criteria for capture antibodies to be included in the panel include a reasonable binding affinity (as determined by a limit of detection below 0.5 µg/mL), low cross-reactivity with antigens of other subtypes, and commercial availability.

Monoclonal IgGs are evaluated as capture antibodies. Both conformational and linear antibodies mAbs are evaluated, and a mix of conformational and linear antibodies are selected for potentially-pandemic influenza A/H1, A/H2 A/H3, A/H5, A/H7, and A/H9. A combination of conformational and neutralizing mAbs against both HA1 and the highly conserved region of HA2 are also selected. One or more antibodies that perform sufficiently targeting a particular subtype of hemagglutinin are included on the universal capture array.

Accordingly, a microarray in accordance with FIG. 1 is prepared, and experimental variables include protein spotting concentrations and conditions, microarray pre-use handling (e.g., washing and blocking), antigen binding time and buffer conditions, label antibody concentration and binding time, and post-labeling wash buffer and conditions.

An appropriate volume of antigen is diluted into blocking buffer (ToC-5531, InDevR Inc.), and the resulting solution is placed directly onto a pre-washed universal capture array. The array is incubated in a humidity chamber at room temperature for one hour. Excess material is removed by pipette and the slides washed. After removal of excess wash solution, the appropriate label is added and incubated at room temperature. Excess label is removed and the slide is washed. Excess liquid is removed prior to imaging on a fluorescence microarray scanner. Quantitative data is extracted using manufacturer's software, and results are processed using an automated algorithm.

The image analysis and quantification algorithm automatically: i) extracts the digital signal from each spot in the image, ii) normalizes the analyte signal to the internal positive control signal, iii) analyzes a matrix of fluorescence signal, spotted antibody concentration, and HA concentration, iv) determines linear response ranges for each spotted antibody concentration when plotted against standard HA concentration (linearity is defined by 4 adjacent points that yield a Pearson's correlation coefficient ($R^2>0.95$) when fit with a linear regression), and v) uses the linear regression fit to back-calculate concentrations for samples of unknown concentration using all of the calibration data in which the fluorescent signal falls within a linear range.

Normalization of the signal on each array using an internal control is used to account for array-to-array variability during manufacture or processing. The internal control is a goat protein capture agent that is subsequently labeled with a fluorescently-tagged mouse anti-goat antibody during the labeling step. The average value from each triplicate spot is divided by the average value from all internal control spots (N>10) and the result multiplied by 100 to adjust for scale. Background averages and standard deviation are obtained from the space between positive control spots, and background values are used to determine the lower limit of detection and quantification.

FURTHER EXAMPLES

1. A method for determining one or more unknown concentrations of hemagglutinin proteins in a sample, the method comprising:
providing one or more substrates comprising at least one microarray, each microarray comprising:
  i. at least one positive control spot,
  ii. at least one negative control spot, and
  iii. at least one subarray, each subarray including a plurality of capture agent spots, each capture agent spot including a murine antibody configured to bind to a linear or conformational epitope of an influenza hemagglutinin protein, wherein a concentration of the antibody in each of the plurality of capture agent spots is substantially the same;
contacting at least one microarray with the sample to form one or more bound complexes, each of the bound complexes comprising a capture agent and an influenza hemagglutinin protein;
generating one or more signals corresponding to an amount of the one or more bound complexes at each spot;
  quantifying the one or more signals to generate one or more quantified signals;
providing one or more calibration curves that establish a one-to-one relationship between a concentration of a reference hemagglutinin protein and the quantified signals; and
comparing the one or more quantified signals to the one or more calibration curves to determine the one or more unknown concentrations of the hemagglutinin proteins in the sample.

2. The method of Example 1, wherein at least one of the sub-array groups targets at least one possible mutation of influenza A hemagglutinin subtype 1.

3. The method of Example 1 or 2, wherein at least one of the sub-array groups targets at least one possible mutation of influenza A hemagglutinin subtype 3.

4. The method of any one of Examples 1 to 3, wherein at least one of the sub-array groups targets at least one possible mutation of Yamagata-lineage influenza B hemagglutinin.

5. The method of any one of Examples 1 to 4, wherein at least one of the sub-array groups targets at least one possible mutation of Victoria-lineage influenza B hemagglutinin.

6. The method of any one of Examples 1 to 5, wherein the microarray comprises at least 4 sub-array groups, one of the at least 4 sub-array groups targeting influenza A hemagglutinin subtype 1, one of the at least 4 sub-array groups targeting influenza A hemagglutinin subtype 3, one of the at least 4 sub-array groups targeting Yamagata-lineage influenza B hemagglutinin, and one of the at least 4 sub-array groups targeting Victoria-lineage influenza B hemagglutinin.

7. The method of any one of Examples 1 to 6, wherein the one or more signals are fluorescence intensities.

8. The method of any one of Examples 1 to 7, wherein the one or more signals are quantified using a microarray scanner.

9. The method of any one of Examples 1 to 8, wherein quantifying the one or more signals includes normalizing the signals as a function of a signal associated with the positive control spot and/or as a function of a signal associated with the negative control spot.

10. The method of any one of Examples 1 to 9, wherein the substrate comprises at least 4 microarrays, at least 6 microarrays, at least 8 microarrays, at least 12 microarrays, least 16 microarrays, at least 24 microarrays, at least 48 microarrays, or 96 microarrays.

11. The method of Example 10, wherein the calibration curves are provided by at least one microarray of the substrate.

12. The method of any one of Examples 1 to 11, wherein the microarrays each include at least 4 subarrays, at least 6 subarrays, at least 8 subarrays, or at least 9 subarrays.

13. The method of any one of Examples 1 to 12, wherein the microarrays comprise at least one antibody capture agent capable of binding to a hemagglutinin associated with a first influenza subtype or lineage, and at least one antibody capture agent capable of binding to a hemagglutinin associated with a second influenza subtype or lineage, and wherein the step of comprising simultaneously determines a concentration of at least one hemagglutinin associated with the first influenza subtype or lineage and a concentration of at least one hemagglutinin associated with the second influenza subtype or lineage.

14. The method of any one of Examples 1 to 13, wherein the microarrays comprise a combination of antibody capture agents specific to a predetermined plurality of influenza subtypes and/or lineages, and wherein the step of generating comprises contacting the bound complexes with a single label agent capable of binding to hemagglutinin associated with each of the predetermined influenza subtypes and/or lineages, and wherein the step of comparing simultaneously determines a concentration of the hemagglutinin proteins from each of the predetermined influenza subtypes and/or lineages.

15. The method of any one of Examples 1 to 14, wherein the microarrays comprise at least one antibody capture agent capable of binding to a conformational epitope of a hemagglutinin protein associated with each of a plurality of predetermined influenza subtypes and/or lineages, and at least one antibody capture agent capable of binding to a linear epitope of the hemagglutinin protein associated with each of the plurality of predetermined influenza subtypes and/or lineages, and wherein the step of comparing simultaneously determines a concentration of the hemagglutinin proteins from each of the predetermined influenza subtypes and/or lineages and optionally further simultaneously determines a stability of the hemagglutinin proteins from each of the predetermined influenza subtypes and/or lineages.

16. The method of any one of Examples 1 to 15, wherein the microarrays comprise at least one neutralizing antibody capture agent capable of binding to a hemagglutinin protein associated with each of a plurality of predetermined influenza subtypes and/or lineages, and at least one non-neutralizing antibody capture agent capable of binding to a hemagglutinin protein associated with each of the plurality of predetermined influenza subtypes and/or lineages, and wherein the step of comparing simultaneously determines a concentration of the hemagglutinin proteins from each of the predetermined influenza subtypes and/or lineages and optionally further simultaneously determines a stability of the hemagglutinin proteins from each of the predetermined influenza subtypes and/or lineages.

17. The method of any one of Examples 1 to 16, wherein the microarrays comprise at least one neutralizing antibody capture agent capable of binding to a conformational epitope of a variable HA1 region of a hemagglutinin protein associated with an influenza strain, and at least one neutralizing antibody capture agent capable of binding to a conformational epitope of a conserved HA2 region of a hemagglutinin protein associated with the influenza strain, and wherein the step of comparing determines a stability of the hemagglutinin protein.

18. The method of 17, wherein the step of generating comprises contacting the bound complexes with a single label agent capable of binding to hemagglutinin associated with each of the predetermined influenza subtypes and/or lineages, and wherein the step of comparing simultaneously determines a concentration and a stability of the hemagglutinin protein.

19. The method of 17, wherein the step of generating comprises contacting the bound complexes with a single label agent capable of binding to hemagglutinin associated with each of the predetermined influenza subtypes and/or lineages, and wherein the step of comparing simultaneously determines a concentration of the hemagglutinin proteins from each of the predetermined influenza subtypes and/or lineages.

20. The method of any one of Examples 1 to 19, wherein the substrate further includes a mask surrounding the microarrays.

21. The method of any one of Examples 1 to 20, wherein the microarray comprises a plurality of capture agents which collectively enable the microarray to detect hemagglutinin proteins associated with an influenza strain over more than one year despite antigenic drift.

22. A device for determining one or more unknown concentrations of one or more hemagglutinin proteins in a sample, the device comprising one or more substrates including at least one microarray, each microarray comprising:
at least one positive control spot;
at least one negative control spot; and
at least one subarray, each subarray including a plurality of capture agent spots, each capture agent spot including a murine antibody configured to bind to a linear or conformational epitope of an influenza hemagglutinin protein, wherein a concentration of the antibody in each of the plurality of capture agent spots is substantially the same.

23. The device of Example 22, wherein at least one of the sub-array groups targets at least one possible mutation of influenza A hemagglutinin subtype 1.

24. The device of Example 22 or 23, wherein at least one of the sub-array groups targets at least one possible mutation of influenza A hemagglutinin subtype 3.

25. The device of any one of Examples 22 to 24, wherein at least one of the sub-array groups targets at least one possible mutation of Yamagata-lineage influenza B hemagglutinin.

26. The device of any one of Examples 22 to 25, wherein at least one of the sub-array groups targets at least one possible mutation of Victoria-lineage influenza B hemagglutinin.

27. The device of any one of Examples 22 to 26, wherein the microarray comprises at least 4 sub-array groups, one of the at least 4 sub-array groups targeting influenza A hemagglutinin subtype 1, one of the at least 4 sub-array groups targeting influenza A hemagglutinin subtype 3, one of the at least 4 sub-array groups targeting Yamagata-lineage influenza B hemagglutinin, and one of the at least 4 sub-array groups targeting Victoria-lineage influenza B hemagglutinin.

28. The device of any one of Examples 22 to 27, wherein the one or more signals are fluorescence intensities.

29. The device of any one of Examples 22 to 28, wherein the device is configured to be analyzed by a microarray scanner.

30. The device of any one of Examples 22 to 29, wherein the substrate comprises at least 4 microarrays, at least 6 microarrays, at least 8 microarrays, at least 12 microarrays,

41 at least 16 microarrays, at least 24 microarrays, at least 48 microarrays, or 96 microarrays.

31. The device of any one of Examples 22 to 30, wherein the microarrays each include at least 4 subarrays, at least 6 subarrays, at least 8 subarrays, or at least 9 subarrays.

32. The device of any one of Examples 22 to 31, wherein the microarrays comprise at least one antibody capture agent capable of binding to a hemagglutinin associated with a first influenza subtype or lineage, and at least one antibody capture agent capable of binding to a hemagglutinin associated with a second influenza subtype or lineage.

33. The device of any one of Examples 22 to 32, wherein the microarrays comprise a combination of antibody capture agents specific to a predetermined plurality of influenza subtypes and/or lineages.

34. The device of any one of Examples 22 to 33, wherein the microarrays comprise at least one antibody capture agent capable of binding to a conformational epitope of a hemagglutinin protein associated with each of a plurality of predetermined influenza subtypes and/or lineages, and at least one antibody capture agent capable of binding to a linear epitope of the hemagglutinin protein associated with each of the plurality of predetermined influenza subtypes and/or lineages.

35. The device of any one of Examples 22 to 34, wherein the microarrays comprise at least one neutralizing antibody capture agent capable of binding to a hemagglutinin protein associated with each of a plurality of predetermined influenza subtypes and/or lineages, and at least one non-neutralizing antibody capture agent capable of binding to a hemagglutinin protein associated with each of the plurality of predetermined influenza subtypes and/or lineages.

36. The device of any one of Examples 22 to 35, wherein the microarrays comprise at least one neutralizing antibody capture agent capable of binding to a conformational epitope of a variable HA1 region of a hemagglutinin protein associated with an influenza strain, and at least one neutralizing antibody capture agent capable of binding to a conformational epitope of a conserved HA2 region of a hemagglutinin protein associated with the influenza strain.

37. The device of any one of Examples 22 to 36 further comprising a mask fluidically separating the microarrays.

38. The device of any one of Examples 22 to 37, wherein the microarray comprises a plurality of capture agents which collectively enable the microarray to detect hemagglutinin proteins associated with an influenza strain over more than one year despite antigenic drift.

These examples thus demonstrate proof of principle for the universal capture array as a new and highly efficient alternative to SRID and ELISA for multiplexed influenza protein quantification in multivalent vaccine formulations. In particular the universal capture array provides means for multiplexed antigen quantification that is able to differentiate and quantify sub-components of multivalent vaccines, that is able to quantify mutated antigens without requiring different reagents be used for each possible mutation (e.g., seasonal), and that is able to measure degradation of the sample without the need for a reference, non-degraded sample. This new protein quantification is also more reliable and simpler to perform than the current SRID or ELISA methods, with comparable or better accuracy and precision.

Although the description above contains many specifics, these should not be construed as limiting the scope of the embodiments but as merely providing illustrations of some of several embodiments. For example, the universal capture array can have any number of spots in any number of configurations; the signal could be attenuation of light; sub-arrays may comprise antibodies that bind conformational or linear epitopes.

Thus the scope of the embodiments should be determined by the appended claims and their legal equivalents, rather than by the examples given.

What is claimed is:

1. A method for determining one or more unknown concentrations of hemagglutinin proteins in a vaccine sample, the method comprising:
providing one or more substrates comprising at least one microarray, each microarray comprising:
i. at least one positive control spot,
ii. at least one negative control spot, and
iii. more than one subarray, each subarray including a plurality of capture agent spots, each capture agent spot including a murine antibody configured to bind to a linear or conformational epitope of an influenza hemagglutinin protein, wherein a concentration of the antibody in each of the plurality of capture agent spots is the same;
contacting at least one microarray with the sample to form one or more bound complexes, each of the bound complexes comprising a capture agent and an influenza hemagglutinin protein;
generating one or more signals corresponding to an amount of the one or more bound complexes at each spot;
quantifying the one or more signals to generate one or more quantified signals;
providing one or more calibration curves that establish a one-to-one relationship between a concentration of a reference hemagglutinin protein and the quantified signals;
comparing the one or more quantified signals to the one or more calibration curves to determine the one or more unknown concentrations of the hemagglutinin proteins in the sample; and
the microarray comprises a plurality of capture agents that are different but related capture agents, wherein a capture agent targets one subset of a class of an antigen in the sample and a different capture agent targets a different subset of the same class of the antigen, wherein the microarray further comprises:
a first subarray having capture agent spots comprising a first anti-A/H1 monoclonal antibody to bind to a first conformational epitope of influenza hemagglutinin;
a second sub-array having capture agent spots comprising a second anti-A/H1 monoclonal antibody to bind to a second conformational epitope of influenza hemagglutinin;
a third sub-array having capture agent spots comprising a first anti-A/H3 monoclonal antibody to bind to a third conformational epitope of influenza hemagglutinin;
a fourth sub-array having capture agent spots comprising a second anti-A/H3 antibody to bind to a fourth conformational epitope of influenza hemagglutinin;
a fifth sub-array having capture agent spots comprising a first anti-B/Yamagata monoclonal antibody to bind to a fifth conformational epitope of influenza hemagglutinin;
a sixth sub-array having capture agent spots comprising a second anti-B/Yamagata monoclonal antibody to bind to a sixth conformational epitope of influenza hemagglutinin;

a seventh sub-array having capture agent spots comprising a first anti-B/Victoria monoclonal antibody to bind to a seventh conformational epitope of influenza hemagglutinin; and an eighth sub-array having capture agent spots comprising a second anti-B/Victoria monoclonal antibody to bind to an eighth conformational epitope of influenza hemagglutinin, wherein the sub-arrays collectively enable the microarray to detect hemagglutinin proteins associated with an influenza of at least one of A/H1, A/H3, B/Yamagata HA or B/Victoria antigen over a period selected from the range of one to six years despite antigenic drift, thereby eliminating a need to change the plurality of capture agents to adapt to seasonal influenza mutations.

2. The method of claim 1, wherein at least one of the sub-array groups targets at least one possible mutation of influenza A hemagglutinin subtype 1.

3. The method of claim 1, wherein at least one of the sub-array groups targets at least one possible mutation of influenza A hemagglutinin subtype 3.

4. The method of claim 1, wherein at least one of the sub-array groups targets at least one possible mutation of Yamagata-lineage influenza B hemagglutinin.

5. The method of claim 1, wherein at least one of the sub-array groups targets at least one possible mutation of Victoria-lineage influenza B hemagglutinin.

6. The method of claim 1, wherein the microarray comprises at least 4 sub-array groups, one of the at least 4 sub-array groups targeting influenza A hemagglutinin subtype 1, one of the at least 4 sub-array groups targeting influenza A hemagglutinin subtype 3, one of the at least 4 sub-array groups targeting Yamagata-lineage influenza B hemagglutinin, and one of the at least 4 sub-array groups targeting Victoria-lineage influenza B hemagglutinin.

7. The method of claim 1, wherein the one or more signals are fluorescence intensities.

8. The method of claim 1, wherein the one or more signals are quantified using a microarray scanner.

9. The method of claim 1, wherein quantifying the one or more signals includes normalizing the signals as a function of a signal associated with the positive control spot and/or as a function of a signal associated with the negative control spot.

10. The method of claim 1, wherein the substrate comprises at least 4 microarrays.

11. The method of claim 10, wherein the calibration curves are provided by at least one microarray of the substrate.

12. The method of claim 1, wherein the microarrays each include at least 4 subarrays.

13. The method of claim 1, wherein the microarrays comprise:
at least one antibody capture agent capable of binding to a hemagglutinin associated with a first influenza subtype or lineage, and
at least one antibody capture agent capable of binding to a hemagglutinin associated with a second influenza subtype or lineage, and
wherein the step of comparing simultaneously determines a concentration of the hemagglutinin associated with the first influenza subtype or lineage and a concentration of the hemagglutinin associated with the second influenza subtype or lineage.

14. The method of claim 1, wherein the microarrays comprise:
a combination of antibody capture agents specific to a predetermined plurality of influenza subtypes and/or lineages, and
wherein the step of generating comprises contacting the bound complexes with a single label agent capable of binding to hemagglutinin associated with each of the predetermined influenza subtypes and/or lineages, and
wherein the step of comparing simultaneously determines a concentration of the hemagglutinin proteins from each of the predetermined influenza subtypes and/or lineages.

15. The method of claim 1, wherein the microarrays comprise:
at least one antibody capture agent capable of binding to a conformational epitope of a hemagglutinin protein associated with each of a plurality of predetermined influenza subtypes and/or lineages,
and at least one antibody capture agent capable of binding to a linear epitope of the hemagglutinin protein associated with each of the plurality of predetermined influenza subtypes and/or lineages, and
wherein the step of comparing simultaneously determines a concentration of the hemagglutinin proteins from each of the predetermined influenza subtypes and/or lineages and further simultaneously determines a stability of the hemagglutinin proteins from each of the predetermined influenza subtypes and/or lineages.

16. The method of claim 1, wherein the microarrays comprise:
at least one neutralizing antibody capture agent capable of binding to a hemagglutinin protein associated with each of a plurality of predetermined influenza subtypes and/or lineages, and
at least one non-neutralizing antibody capture agent capable of binding to a hemagglutinin protein associated with each of the plurality of predetermined influenza subtypes and/or lineages, and
wherein the step of comparing simultaneously determines a concentration of the hemagglutinin proteins from each of the predetermined influenza subtypes.

17. The method of claim 1, wherein the microarrays comprise:
at least one neutralizing antibody capture agent capable of binding to a conformational and linear epitope of a variable HA1 region of a hemagglutinin protein associated with an influenza strain, and
at least one neutralizing antibody capture agent capable of binding to a conformational and linear epitope of a conserved HA2 region of a hemagglutinin protein associated with the influenza strain, and
wherein the step of comparing determines a stability of the hemagglutinin protein.

18. The method of 17, wherein the step of generating comprises contacting the bound complexes with a single label agent capable of binding to hemagglutinin associated with each of the predetermined influenza subtypes and/or lineages, and wherein the step of comparing simultaneously determines a concentration and a stability of the hemagglutinin protein.

19. The method of 17, wherein the step of generating comprises contacting the bound complexes with a single label agent capable of binding to hemagglutinin associated with each of the predetermined influenza subtypes and/or lineages, and wherein the step of comparing simultaneously determines a concentration of the hemagglutinin proteins from each of the predetermined influenza subtypes and/or lineages.

20. The method of claim 1, wherein the substrate further includes a mask surrounding the microarrays.

21. The method of claim 1, wherein the vaccine sample is a multivalent annual influenza vaccine comprising antigens from the influenza subtypes A/H1 and A/H3, and lineages B/Yamagata HA and B/Victoria, and the method simultaneously differentiates and quantifies antigens associated with each of the influenza subtypes A/H1 and A/H3, and lineages B/Yamagata HA and B/Victoria.

22. The method of claim 1, wherein the vaccine sample is a monovalent formulation for use as a component in a multivalent influenza vaccine.

23. The method of claim 1, wherein the microarray further comprises:
- capture agent spots comprising a third anti-A/H1 antibody to bind to a first linear epitope of influenza hemagglutinin; and/or
- capture agent spots comprising a third anti-A/H3 antibody to bind to a second linear epitope of influenza hemagglutinin.

* * * * *